United States Patent
Colby et al.

(10) Patent No.: US 9,908,837 B2
(45) Date of Patent: Mar. 6, 2018

(54) METHOD FOR PREPARING (METH)ACRYLATES OF BIOBASED ALCOHOLS AND POLYMERS THEREOF

(71) Applicant: 3M INNOVATIVE PROPERTIES COMPANY, St. Paul, MN (US)

(72) Inventors: Joshua L. Colby, Lino Lakes, MN (US); Aaron E. Hutt, St. Paul, MN (US); Terence D. Spawn, Stillwater, MN (US); Jason D. Clapper, Lino Lakes, MN (US); Tabitha A. Clem, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 14/769,850

(22) PCT Filed: Mar. 13, 2014

(86) PCT No.: PCT/US2014/025169
§ 371 (c)(1),
(2) Date: Aug. 24, 2015

(87) PCT Pub. No.: WO2014/151179
PCT Pub. Date: Sep. 25, 2014

(65) Prior Publication Data
US 2016/0009628 A1   Jan. 14, 2016

Related U.S. Application Data

(60) Provisional application No. 61/789,246, filed on Mar. 15, 2013.

(51) Int. Cl.
*C07C 1/24* (2006.01)
*C07C 11/02* (2006.01)
*C07C 67/04* (2006.01)
*C07C 69/54* (2006.01)
*C08F 220/06* (2006.01)
*C08F 220/18* (2006.01)
*C09J 133/08* (2006.01)

(52) U.S. Cl.
CPC ............... *C07C 67/04* (2013.01); *C07C 1/24* (2013.01); *C08F 220/18* (2013.01); *C09J 133/08* (2013.01); *C07C 2531/08* (2013.01); *C07C 2531/10* (2013.01)

(58) Field of Classification Search
CPC ...................................................... C07C 67/04
See application file for complete search history.

(56) References Cited

U.S. PATENT DOCUMENTS

| 3,037,052 | A | * | 5/1962 | Bortnick | ................. B01J 31/10 521/26 |
| 3,691,140 | A | | 9/1972 | Silver | |
| 4,166,152 | A | | 8/1979 | Baker | |
| 4,619,979 | A | | 10/1986 | Kotnour | |
| 4,636,432 | A | | 1/1987 | Shibano | |
| 4,656,218 | A | | 4/1987 | Kinoshita | |
| 4,792,620 | A | * | 12/1988 | Paulik | ................. B01J 31/0231 560/232 |
| 4,843,134 | A | | 6/1989 | Kotnour | |
| 5,045,569 | A | | 9/1991 | Delgado | |
| 5,602,221 | A | | 2/1997 | Bennett | |
| 5,637,646 | A | | 6/1997 | Ellis | |
| 5,804,610 | A | | 9/1998 | Hamer | |
| 7,385,020 | B2 | | 6/2008 | Anderson | |
| 7,893,179 | B2 | | 2/2011 | Anderson | |
| 8,440,873 | B2 | | 5/2013 | Bailey | |
| 2012/0220808 | A1 | * | 8/2012 | Takada | ................. B01J 21/04 585/639 |
| 2012/0271089 | A1 | | 10/2012 | Wright | |
| 2012/0329898 | A1 | | 12/2012 | Weikel | |

FOREIGN PATENT DOCUMENTS

| BE | 540049 | 8/1955 |
| DE | 102009017827 | 10/2010 |
| WO | WO 2007-003901 | 1/2007 |
| WO | WO 2008-066577 | 6/2008 |
| WO | WO 2009-079213 | 6/2009 |
| WO | WO 2009/079213 A2 * | 6/2009 |
| WO | WO 2010-121591 | 10/2010 |
| WO | WO 2011-037681 | 3/2011 |
| WO | WO 2012-088126 | 6/2012 |

OTHER PUBLICATIONS

Norskov et al, Nature Chemistry, Towards the Computational Design of Solid Catalysts, 2009, 1, pp. 37-46.*
ASTM D6866-12, "Standard Test Methods for Determining the Biobased Content of Solid, Liquid, and Gaseous Samples Using Radiocarbon Analysis", 14 pgs.
Bringue, "Study of the Chemical Equilibrium of the Liquid-Phase Dehydration of 1-Hexanol to Dihexyl Ether", Journal of Chemical Engineering Data, 2008, vol. 53, No. 12, pp. 2854-2860.
Bringue, "Thermally stable ion-exchange resins as catalysts for the liquid-phase dehydration of 1-pentanol to di-*n*-pentyl ether (DNPE)", Journal of Catalysis, 2006, vol. 244, No. 1, pp. 33-42.
Changi, "Reaction kinetics and pathways for phytol in high-temperature water", Chemical Engineering Journal, 2012, vol. 189-190, pp. 336-345.
Liu, "Efficient homogeneous catalysis of heteropoly acid and its characterization through etherifications of alcohol", Journal of Molecular Catalysis A: Chemical, 2001, vol. 170, pp. 109-115.

(Continued)

*Primary Examiner* — Paul A Zucker
(74) *Attorney, Agent, or Firm* — Adrian L. Pishko

(57) ABSTRACT

Polymers, particularly those used in pressure-sensitive adhesives, are prepared from a mixture of structural isomers of a secondary alkyl (meth)acrylate monomer. The mixture is made by dehydrating a biobased $C_2$-$C_{22}$ alcohol with a first acid catalyst using a continuous process to form a mixture of olefins, and reacting (meth)acrylic acid with at least some of the mixture of olefins in the presence of a second acid catalyst. The adhesives are characterized by exhibiting an overall balance of adhesive and cohesive characteristics, and containing biobased material.

7 Claims, 1 Drawing Sheet

(56) References Cited

OTHER PUBLICATIONS

Ren, "Selective Hydrodeoxygenation of Biomass-Derived Oxygenates to Unsaturated Hydrocarbons using Molybdenum Carbide Catalysts", ChemSusChem Communications, 2013, vol. 6, pp. 798-801.
Tanabe, "Industrial application of solid acid-base catalysts", Applied Catalysis A: General, 1999, vol. 181, pp. 399-434.
International Search Report for PCT International Application No. PCT/US2014/027756, dated Aug. 21, 2014, 4pgs.
International Search Report for PCT International Application No. PCT/US2014/025169, dated Jun. 11, 2014, 4pgs.

\* cited by examiner

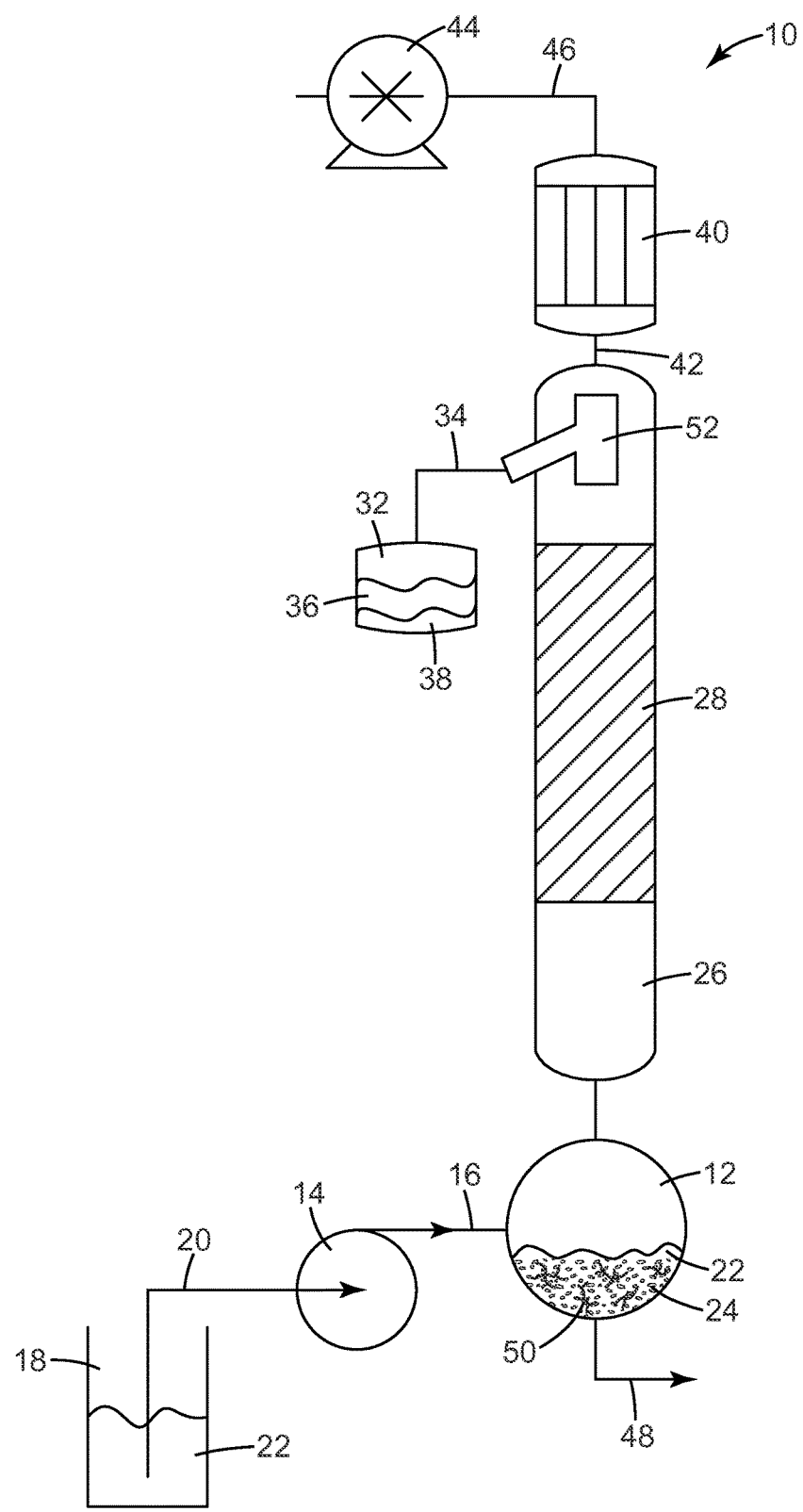

METHOD FOR PREPARING (METH)ACRYLATES OF BIOBASED ALCOHOLS AND POLYMERS THEREOF

CROSS REFERENCE TO RELATED APPLICATIONS

This application is a national stage filing under 35 U.S.C. 371 of PCT/US2014/025169, filed Mar. 14, 2014, which claims priority to U.S. Application No. 61/789,246, filed Mar. 15, 2013, the disclosure of which is incorporated by reference in its/their entirety herein.

TECHNICAL FIELD

The present disclosure relates to selectively synthesizing a mixture of olefins including dehydration of biobased alcohols. The olefins can be used to make polymers, for example pressure-sensitive adhesives.

BACKGROUND

Pressure-sensitive adhesive tapes are virtually ubiquitous in the home and workplace. In its simplest configuration, a pressure-sensitive adhesive tape comprises an adhesive and a backing, and the overall construction is tacky at the use temperature and adheres to a variety of substrates using only moderate pressure to form the bond. In this fashion, pressure-sensitive adhesive tapes constitute a complete, self-contained bonding system.

There are a wide variety of pressure-sensitive adhesive (PSA) materials available today that include natural crude or synthetic rubbers, block copolymers, and (meth)acrylic-based polymeric compositions. (Meth)acrylic-based PSAs in particular have been the focus of a great deal of development over the last half century as the performance demands for PSAs have increased. (Meth)acrylic-based PSAs may be closely tailored to provide a number of desired attributes such as elasticity, tackiness, transparency, resistance to oxidation and sunlight, etc., as well as to have the necessary degree of adhesion and cohesion for demanding tape applications. The (meth)acrylic-based PSAs are usually (meth)acrylic ester PSAs, which are also referred to as (meth)acrylate PSAs or PSA (meth)acrylates. That is, these PSAs include a poly(meth)acrylate material.

SUMMARY

The present disclosure provides a solution to the problems associated with preparing polymers from exclusively petroleum feedstocks, particularly polymers used in pressure-sensitive adhesives (PSAs).

In a first embodiment, the present disclosure provides a method of making a mixture of structural isomers of a secondary alkyl (meth)acrylate of Formula (I):

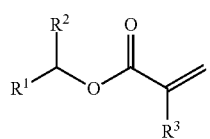

(I)

$R^1$ and $R^2$ are each independently a $C_1$ to $C_{20}$ saturated linear alkyl group, the sum of the number of carbons in $R^1$ and $R^2$ is 2 to 21, and $R^3$ is H or $CH_3$. The method includes dehydrating a biobased $C_2$-$C_{22}$ alcohol with a first acid catalyst using a continuous process to form a mixture of olefins, and reacting (meth)acrylic acid with at least some of the mixture of olefins in the presence of a second acid catalyst.

In a second embodiment, the present disclosure provides a mixture of $C_2$-$C_{22}$ olefins, where the olefins are biobased as determined using ASTM D6866-12.

In a third embodiment, the present disclosure provides a pressure-sensitive adhesive composition including a (meth)acrylate polymer comprising interpolymerized monomers made from a mixture of olefins. Eighty percent to 100% by weight of the mixture of olefins are biobased olefins, as determined using ASTM D6866-12.

In a fourth embodiment, the present disclosure provides a mixture of olefins made by a method including reacting a $C_2$-$C_{22}$ primary alcohol with an acid catalyst at a temperature of 150° C. to 190° C.

In a fifth embodiment, the present disclosure provides a method of making a mixture of olefins including reacting a secondary alcohol with an acid catalyst at a temperature of 100° C. to 190° C. The secondary alcohol is a biobased alcohol, as determined using ASTM D6866-12.

In a sixth embodiment, the present disclosure provides a method of making a mixture of olefins including reacting a $C_2$-$C_{22}$ primary alcohol with an acid catalyst at a temperature of 150° C. to 190° C. The reaction is performed in a continuous reactor at a constant weight hourly space velocity (WHSV) of 0.5 $h^{-1}$ to 10 $h^{-1}$, where the WHSV is a ratio of mass flow of the $C_2$-$C_{22}$ primary alcohol entering the system per hour to the mass of the catalyst material.

Various unexpected results and advantages are obtained in exemplary embodiments of the disclosure. One such advantage of exemplary embodiments of the present disclosure is that mixtures of biobased olefins are produced quickly using a selective method of dehydrating plant-derived alcohols, for example by using a continuous method employing an acid catalyst. The dehydration reaction contributes to the rate of production of the mixtures of olefins by increasing yield of and selectivity to the olefins, which would typically be minor intermediate byproducts generated during the dehydration of alcohols by an acid catalyst. Further, in embodiments in which the acid catalyst comprises a heterogeneous catalyst, the process does not require catalyst neutralization and/or filtration steps.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The disclosure may be more completely understood in consideration of the following detailed description of various embodiments of the disclosure in connection with the accompanying figures, in which:

FIG. 1 is a flow diagram of a method for selectively producing olefins from an alcohol according to an exemplary embodiment of the present disclosure.

While the above-identified drawing, which may not be drawn to scale, set forth an embodiment of the present disclosure, other embodiments are also contemplated, as noted in the Detailed Description.

DETAILED DESCRIPTION

Pressure sensitive adhesives (PSAs) are known to possess properties including the following: (1) aggressive and permanent tack, (2) adherence with no more than finger pressure, (3) sufficient ability to hold onto an adherend or substrate, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These adhesive characteristics are assessed generally by means of tests which are designed to individually measure tack, adhesion (peel strength), and cohesion (shear holding power), as noted in A. V. Pocius in *Adhesion and Adhesives Technology: An Introduction*, $2^{nd}$ Ed., Hanser Gardner Publication, Cincinnati, OH, 2002. These measurements taken together constitute the balance of properties often used to characterize a PSA.

With broadened use of pressure-sensitive adhesive tapes over the years, performance requirements have become more demanding. Shear holding capability, for example, which originally was intended for applications supporting modest loads at room temperature, has now increased substantially for many applications in terms of operating temperature and load. So-called high performance pressure-sensitive adhesive tapes are those capable of supporting loads at elevated temperatures for 10,000 minutes. Increased shear holding capability has generally been accomplished by crosslinking the PSA, although considerable care must be exercised so that high levels of tack and adhesion are retained in order to retain the aforementioned balance of properties.

Central to all PSAs is a desired balance of adhesion and cohesion that is often achieved by optimizing the physical properties of the acrylic elastomer, such as glass transition temperature and modulus. For example, if the glass transition temperature ($T_g$) or modulus of the elastomer is too high, the Dahlquist criterion for tack (storage modulus less than $3 \times 10^6$ dynes/cm$^2$ at room temperature and oscillation frequency of 1 Hz) will not be met, and the material will not be tacky and is not useful by itself as a PSA material. Often in this case, low molecular weight, high $T_g$ resin polymers (tackifiers) or low molecular weight, low $T_g$ polymers (plasticizers) are used to modulate the $T_g$ and modulus into an optimal PSA range.

(Meth)acrylic ester PSAs of today are typically an elastomeric polymer prepared using a low $T_g$ non-polar monomer. Two widely used low $T_g$ acrylates in PSAs are 2-ethylhexyl acrylate (EHA) and isooctyl acrylate (IOA), each providing an alkyl chain of eight carbon atoms ($C_8$). Longer or shorter alkyl chains have a number of disadvantages in terms of PSA performance. For example, shorter alkyl chain (e.g., butylacrylate-$C_4$) will significantly increase both the $T_g$ and modulus of the elastomer, possibly increasing the room temperature storage modulus above $3 \times 10^6$ dynes/cm$^2$. Alternatively, longer linear alkyl chains (e.g., octadecyl acrylate-$C_{18}$) can lead to crystalline groups within the polymer that will also significantly reduce its degree of tack.

Further, acrylic PSAs are generally derived from petroleum feedstocks. The increase in the price of oil, and concomitant petroleum-derived products, has led to volatile prices and supply for many adhesive products. It is desirable to replace all or part of the petroleum-based feedstocks with those derived from renewable sources, such as plants, as such materials become relatively cheaper, and are therefore both economically and socially beneficial. Therefore, the need for such plant-derived materials has become increasingly significant.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

As used in this specification and the appended embodiments, the singular forms "a", "an", and "the" include plural referents unless the content clearly dictates otherwise. Thus, for example, reference to fine fibers containing "a compound" includes a mixture of two or more compounds. As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "(co)polymer" is inclusive of both homopolymers containing a single monomer and copolymers containing two or more different monomers.

The term "(meth)acrylic" or "(meth)acrylate" is inclusive of both acrylic and methacrylic (or acrylate and methacrylate). As used herein "$C_1$-$C_{22}$ alkanol (meth)acrylate" refers to a (meth)acrylate ester of a $C_1$-$C_{22}$ alkanol.

The term "aliphatic group" means a saturated or unsaturated linear or branched hydrocarbon group. This term is used to encompass alkyl, alkenyl, and alkynyl groups, for example.

The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkylene group" refers to a divalent alkyl group.

The term "heteroalkyl group" means an alkyl group having at least one —CH$_2$— replaced with a heteroatom such as O or S. In many embodiments, the heteroalkyl group is a monovalent polyether group. The term "heteroalkylene group" refers to a divalent heteroalkyl group. In many embodiments, the heteroalkylene group is a divalent polyether group.

The term "alicyclic group" means a cyclic hydrocarbon group having properties resembling those of aliphatic groups. The term "aromatic group" or "aryl group" means a mono-or polynuclear aromatic hydrocarbon group.

When a group is present more than once in a formula described herein, each group is "independently" selected, whether specifically stated or not. For example, when more than one R group is present in a formula, each R group is independently selected.

The term "continuous" process refers to a process with non-interrupted flow or semi-non-interrupted flow (i.e., pulsed flow) of material(s) in and out of the reactor once the system is operating at steady state. Preferably, a "continuous reactor" refers to a reactor comprising a heterogeneous catalyst, which may be a flow-through system. In a continuous process of this disclosure, a reactor, having an inlet for reactants and at least one outlet for products, is charged with an acid catalyst (e.g., a solid acid catalyst) and used to perform the desired chemical transformation(s) under conditions of continuous stirring. This reactor configuration, often described as a "continuous stirred tank reactor," can be advantageous when compared to homogeneously catalyzed batch reactions for a number of reasons including: ease of reaction and tighter control over process variables (e.g., temperature, pressure and residence time). Moreover, the use of heterogeneous catalysts can be advantageous when compared to homogeneous catalysts due to eliminating the chance of volatilizing the catalyst out of the reaction solution, providing a higher catalyst to reagent/reactant ratio (facilitating higher rates of reaction) without a concomitant increase in cost, and eliminating any catalyst filtration and/or neutralization step. Preferably, one outlet of the reactor, for products, preferably includes a distillation column for separation of one or more of the reaction products from other components present in the reactor. Unless stated otherwise, the reactions disclosed herein are not diluted, and it will be understood by the skilled practitioner that the inclusion of one or more diluents in a reactor may decrease the rate of reaction as compared to no diluent present in the reactor.

As an alternative to using a continuous stirred tank reactor configuration, other well known continuous reactor configurations may potentially be employed such as "reactive distillation" reactors or "packed-bed" reactors. For example, a "reactive distillation" reactor refers to a reactor comprising a distillation column packed with a catalyst. The reaction is catalyzed as reactants interact with the catalyst within the length of the distillation column.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

A wide variety of commercially available solid (typically, resin) acid catalysts may be used with a continuous stirred tank reactor, for example, in a continuous process. In particular, solid acid (heterogeneous) catalysts may be advantageously used in performing the desired chemical transformation(s) disclosed herein including, but not limited to, sulfonated styrene divinylbenzene copolymers (e.g., those available under the trade name AMBERLYST, for instance AMBERLYST 70 or AMBERLYST 36) and high fluorine content aliphatic sulfonic acids (e.g., those available under the trade name NAFION). Selection of a suitable solid acid catalyst material is typically determined by cost, rate of reaction, and selectivity to desired products. One particular type of resin, macroreticular resin, is particularly preferred because it is inexpensive and available in a wide variety of different physical and/or chemical structures. Varying catalyst features such as catalyst surface area, porosity, and acidity can be tuned by varying resin properties such as the extent of crosslinking and degree of sulfonization, facilitating the selection of a suitable catalyst for each desired reaction. Selection of such features is within the skill of one skilled in the art.

AMBERLYST 70 is one suitable cation exchange resin, and has a halogenated interface between the sulfonic acid catalyst group and the polymer resin that provides temperature stability, and may also affect reactivity. AMBERLYST 36 is another suitable cation exchange resin, which has a lower maximum operating temperature than AMBERLYST 70. The rate of reaction using AMBERLYST 36 will likely be slower than using AMBERLYST 70, due at least to the decreased maximum reaction temperature.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

In one embodiment, the present disclosure provides a method of making a mixture of structural isomers of a secondary alkyl (meth)acrylate of Formula (I):

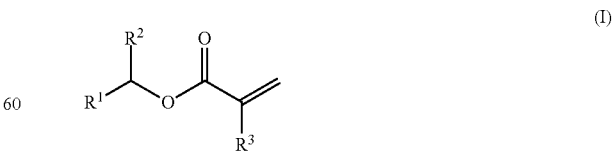

wherein:
R$^1$ and R$^2$ are each independently a C$_1$ to C$_{20}$ saturated linear alkyl group (it will be understood that in this formula R$^1$ and R$^2$ are not joined together to form a ring); the sum of the number of carbons in $R^1$ and $R^2$ is 2 to 21; and $R^3$ is H or $CH_3$.

wherein the method comprises: dehydrating a biobased $C_2$-$C_{22}$ alcohol with a first acid catalyst using a continuous process, thereby forming a mixture of olefins; and reacting (meth)acrylic acid with the mixture of olefins in the presence of a second acid catalyst.

Thus, in one exemplary embodiment, the disclosure provides a method of making a mixture of olefins comprising dehydrating an alcohol with a first acid catalyst, for example and without limitation, comprising a sulfonic acid, in a continuous process. Olefins from petroleum feedstocks are known reactants to produce more valuable compounds, such as alcohols and ethers, via hydrogenation reactions. In particular, Bringué et al. (*J. Chem. Eng. Data*, vol. 53, (2008), 2854-2860) report that the production of ethers from linear olefins is promising due to substituting the ethers for undesirable olefins in diesel fuel, for instance. Although the reaction scheme proposed by Bringué et al. shows olefin isomers as minor reaction byproducts of the batch dehydration of 1-hexanol to dipentyl ether at equilibrium, there is no disclosure regarding selectively producing olefins, in either a batch or continuous process. Moreover, there would not have been any reason to dehydrate alcohols to olefins at least because olefins are the original starting materials (i.e., the alcohols of Bringué et al. are disclosed to be produced by hydroformylation and hydrogenation of $C_4$ and $C_5$ linear olefins).

Without wishing to be bound by theory, a proposed global reaction mechanism for dehydrating an alcohol to a mixture of olefins is as follows:

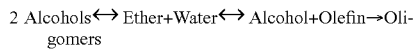

For example, a general proposed structural reaction is provided below as Scheme I.

Scheme I

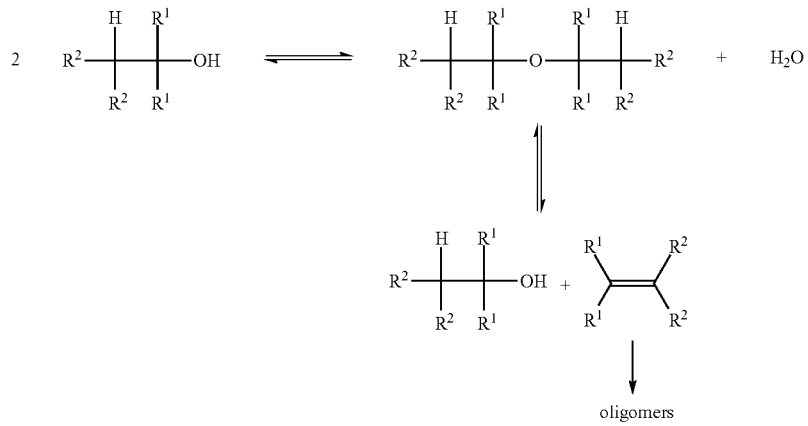

wherein each of the two $R^1$s and each of the $R^2$s are independently selected from H and $C_1$-$C_{20}$ aliphatic groups. Moreover, the product olefin isomerizes when the chain length of the olefin is greater than two carbons.

Accordingly, olefin isomers are one of several potential intermediate products, whereas any oligomers that form are terminal, or irreversible final products. Methods of the present invention provide selective continuous dehydration of biobased alcohols to produce a mixture of olefin isomers. Selectivity is achieved in part by collecting the olefins produced as the reaction takes place, which drives the equilibrium towards producing olefins and minimizes the opportunity for olefins to react with the catalyst and form oligomers. Moreover, the temperature is selected to assist in driving the equilibrium towards producing olefins.

Referring to FIG. 1, embodiments of the method comprise a system 10, in which a reaction vessel 12 is charged with an acid catalyst 24, followed by feeding an alcohol 22 to the reaction vessel 12 from a reactant source container 18. The alcohol 22 is fed from the container 18, optionally through feed tubing 20 using a feed pump 14 then through delivery tubing 16. The alcohol 22 is preferably fed continuously, then controlled in the reaction vessel 12 at a predetermined temperature and pressure. The temperature is typically 150° C. to 190° C., for example.

As the dehydration reaction of the alcohol 22 progresses in the reaction vessel 12, products including ethers, water 38, olefins 36, alcohol 22 and oligomers 50 (e.g., oligomerized olefins) may all be produced in the reaction vessel 12. The reaction vessel 12 is fitted with a column 26 either directly attached to the reaction vessel 12 or via a suitable connector. For example, olefins 36 produced during the dehydration reaction between the alcohol 22 and the acid catalyst 24 will boil out of the reaction mixture and travel up the column 26. Product olefins 36 and water 38 are collected in a collection flask 32, in two phases. The mixture of olefins 36 are readily separated from the water 38 by density, for instance using a separatory funnel In certain embodiments, diluents can be added to the reaction vessel 12, for instance diluents such as alcohols or alkanes. Preferably, these components are unreactive diluents. The diluents optionally have slightly higher boiling points than the product olefins 36. The column 26 preferably contains packing 28 to minimize collection of components other than the olefins 36 and water 38 that evaporate at the reaction temperature(s) within the reaction vessel 12, such as alcohols. The flow diagram in FIG. 1 also illustrates a reflux valve 52 provided on the column 26. The reflux valve 52 controls the amount of product that is sent to the collection flask 32 and the amount of product (including alcohols) that is returned to the column 26. Collection tubing 34 is optionally employed between the reflux valve 52 and the collection flask 32, to prevent any product loss between the two equipment components.

In some embodiments, a condenser 40 is provided on the column 26 to condense volatile products from the gas phase to the liquid phase. The condenser 40 may be directly attached to the column 26 (not shown) or via a connector 42. A vacuum pump 44 is further provided to draw volatile products out of the reaction vessel 12, and the pump 44 is preferably connected to the condenser 40 via pump tubing 46.

In several embodiments, removal tubing 48 is provided to remove any oligomers 50 or other impurities from the reaction vessel 12. For example, the removal tubing 48 is optionally connected to a lower portion of the reaction vessel 12 to expedite removal of the undesirable reaction products.

In certain embodiments, the product olefins 36 are separated from the water 38 and reacted with meth(acrylic acid) in the presence of an acid catalyst, thereby forming a mixture of structural isomers of a secondary alkyl(meth) acrylate having structures as described herein. The reaction of the product olefins 36 is optionally performed using a continuous tubular reactor packed with the acid catalyst (not shown).

The biobased alcohol is dehydrated after entering the reaction zone, defined to be the volume in the reactor occupied by the heterogeneous catalyst material. Time required to perform the desired reaction can vary, primarily due to catalyst type, temperature, and reactant concentration. Reactant residence time, defined as the liquid volume in the reactor divided by the volumetric feed rate of the reactants, may be controlled, for example, by adjusting the total reactant feed rate to the reactor. Reactant residence time is typically held constant at values of at least 1 minute, and often at least 5 minutes. Reactant residence time is typically held constant at values of no greater than 120 minutes, and often no greater than 20 minutes. Reaction temperatures may be controlled with resistively heated insulating tape or by circulating heating oil from a temperature controlled bath, or other conventional methods. In most embodiments, the mixture of olefins is continuously removed from the reactor, for instance through a packed distillation column.

For example and without limitation, during use a biobased $C_2$-$C_{22}$ alcohol is added to a continuous reactor containing an acid catalyst stable to temperatures as high as 190° C. The biobased $C_2$-$C_{22}$ alcohol is not particularly limited, and is optionally selected from the group consisting of $C_2$ alcohols, $C_3$ alcohols, $C_4$ alcohols, $C_5$ alcohols, $C_6$ alcohols, $C_7$ alcohols, $C_8$ alcohols, $C_9$ alcohols, $C_{10}$ alcohols, $C_{11}$ alcohols, $C_{12}$ alcohols, $C_{13}$ alcohols, $C_{14}$ alcohols, $C_{15}$ alcohols, $C_{16}$ alcohols, $C_{17}$ alcohols, $C_{18}$ alcohols, $C_{19}$ alcohols, $C_{20}$ alcohols, $C_{21}$ alcohols, $C_{22}$ alcohols, and mixtures thereof. In certain embodiments, the $C_2$-$C_{22}$ alcohol comprises a $C_8$ alcohol, for instance 1-octanol, 2-octanol, 3-octanol, or 4-octanol.

With respect to structure, the $C_2$-$C_{22}$ alcohol optionally comprises a primary alcohol, a secondary alcohol, a tertiary alcohol, a branched alcohol, a linear alcohol, a saturated alcohol, an unsaturated alcohol, or a combination thereof.

In many embodiments, the dehydration of a biobased alcohol to produce a mixture of olefins is performed in a continuous reactor at a weight hourly space velocity (WHSV) of 0.1 hour$^{-1}$ (h$^{-1}$) (2.8×10$^{-5}$ seconds$^{-1}$) to 3 h$^{-1}$ (8.3×10$^{-4}$ s$^{-1}$), or 0.3 h$^{-1}$ (8.3×10$^{-4}$ s$^{-1}$) to 1 h$^{-1}$ (2.8×10$^{-4}$ s$^{-1}$), or 0.5 h$^{-1}$ (1.4×10$^{-4}$ s$^{-1}$) to 1.5 h$^{-1}$ (4.2×10$^{-4}$ s$^{-1}$), or 0.5 h$^{-1}$ (1.4×10$^{-4}$ s$^{-1}$) to 2 h$^{-1}$ (5.6×10$^{-4}$ s$^{-1}$), or 0.2 h$^{-1}$ (5.6×10$^{-5}$ s$^{-1}$) to 0.7 h$^{-1}$ (1.9×10$^{-4}$ s$^{-1}$). The WHSV, as used herein, is defined as a ratio of the mass flow of the $C_2$-$C_{22}$ alcohol entering the system per hour, to the mass of the acid catalyst in the continuous reactor. It is to be understood that the phrase "the mass of the acid catalyst" as used throughout this disclosure refers to the mass of the entire catalyst material (i.e., including both the support structure and the acid functional groups for a heterogeneous acid catalyst). In other words, the WHSV is a ratio of mass flow of the $C_2$-$C_{22}$ primary alcohol entering the system per hour to the mass of the catalyst material.

In other terms, in certain embodiments a combination of the mixture of olefins and water is produced at a rate of 0.5 g h$^{-1}$ (1.4×10$^{-4}$ g s$^{-1}$) to 10 g h$^{-1}$ (2.8×10$^{-3}$ g s$^{-1}$) per gram of the acid catalyst, or at a rate of 1 g h$^{-1}$ (2.8×10$^{-4}$ g s$^-$) to 5 g h$^{-1}$ (1.4×10$^{-4}$ g s$^{-1}$) per gram of the acid catalyst (i.e., per gram of the catalyst material). Moreover, in many embodiments at least 75%, or at least 85%, or at least 90%, or at least 95% of the $C_2$-$C_{22}$ alcohol by weight is recovered as a combination of the mixture of olefins and water.

In certain embodiments the acid catalyst comprises a heterogeneous acid catalyst, for example and without limitation a cation exchange resin. As noted above, suitable cation exchange resins include those commercially available from Dow Chemical Company (Midland, Mich.) under the trade name AMBERLYST. In certain embodiments, AMBERLYST 70 is a particularly preferred heterogeneous acid catalyst. In some embodiments the acid catalyst comprises a material such as a polymer, zeolite, or other solid structural material having acidic functional groups affixed thereto. Suitable acid catalysts comprise acidic functional groups, such as comprising sulfonic acid.

At high acid catalyst activity and high temperatures, it was discovered that alcohols could be more rapidly dehydrated to olefins than ethers, although the catalyst activity and high temperatures also drive the olefins to oligomerize. Without wishing to be bound by theory, it is further believed that the inclusion of water in the reactor can improve selectivity to the olefin isomers, as compared to the same reaction absent water, due to the decrease in rate of olefin oligomerization. Moreover, the rate of reaction is substantially maintained when water is added to the reactor. Without wishing to be bound by theory, it is believed that the water decreases the effective acidity of the acid functional groups of the acid catalyst by hydrating the acid functional groups, thereby decreasing the activity of the acid catalyst. Alternatively, an unreactive diluent may be included in the reactor to dilute the acid functional groups of the acid catalyst to minimize the occurrence of olefin molecules reacting and oligomerizing in the reactor. The diluent optionally also boils out of the reactor during the dehydration process. Preferably, diluents are non-reactive diluents, more preferably non-reactive volatile organic solvents such as alkanes, aromatics, and/or alcohols, which have higher boiling points than the particular olefins produced. In certain embodiments, water comprises 0.1 to 10 percent by weight of the total reactants, or 0.1 to 5 percent by weight, or 1 to 5 percent by weight, or 1 to 3 percent by weight, or 2 to 4 percent by weight of the total reactants. In certain embodiments, a diluent comprises 0.1 to 95 percent by weight of the total reactants, or 0.1 to 80 percent by weight, or 10 to 50 percent by weight, or 1 to 30 percent by weight, or 50 to 90 percent by weight of the total reactants.

As noted above, the alcohol reactant is biobased. ASTM D6866-12, "Determining the Biobased Content of Solid, Liquid, and Gaseous Samples Using Radiocarbon Analysis," provides methods for determining the source of carbon in a material using carbon dating. In particular, $^{14}C/C$ and $^{13}C/C$ isotopic ratios indicate if a material has a fossil (e.g., petroleum based) carbon source or a plant based carbon source. A material with a fossil carbon source contains no $^{14}$C, whereas a material with 100% $^{14}$C (after correction for 1950s nuclear testing) indicates a completely modern, biobased carbon source. In most embodiments, the mixture of olefins comprises between 70% and 100% by weight biobased carbon, as determined using ASTM D6866-12, or between 80% and 100% by weight biobased carbon, or between 95% and 100% by weight biobased carbon.

Alternatively, the biobased content of the alcohol, for instance 1-octanol or 2-octanol, employed in the esterification reaction is expressed as a $^{14}$C/C ratio. In certain embodiments, the alcohol comprises a $^{14}$C/C ratio of $1.0 \times 10^{-14}$ or higher, or of $1.0 \times 10^{-13}$ or higher, or of $1.0 \times 10^{-12}$ or higher.

The biobased $C_2$-$C_{22}$ alcohol is preferably derived from at least one plant oil selected from the group consisting of almond oil, castor oil, coconut oil, soybean oil, rapeseed oil, cottonseed oil, sunflower seed oil, groundnut oil, palm oil, palm kernel oil, sesame oil, linseed oil, maize oil and coconut oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, and combinations thereof.

In certain embodiments, biobased 2-octanol is derived from at least one plant oil, for example from castor oil. The 2-octanol may be prepared by treatment of ricinoleic acid, derived from castor oil, (or an ester or acyl halide thereof) with sodium hydroxide, followed by distillation from the co-product sebacic acid. A suitable biobased 2-octanol is commercially available from Alfa Aesar, Ward Hill, Mass.

The method of certain embodiments producing a mixture of olefins further comprises recycling alcohol back to the reactant feed. Typically, the mixture of olefins produced is further processed, for example by purifying the olefin isomers following separation from water collected in the product collection flask. Whether or not the mixture of olefins produced is purified, at least some of the mixture of olefins is preferably reacted with (meth)acrylic acid in the presence of an acid catalyst, thereby forming a mixture of structural isomers of a secondary alkyl (meth)acrylate.

In another exemplary embodiment, the disclosure provides a mixture of $C_2$-$C_{22}$ olefins, wherein the olefins are biobased as determined using ASTM D6866-12. In an embodiment, the olefins comprise a single unsaturation, while in another embodiment the olefins comprise multiple unsaturations. The mixture of $C_2$-$C_{22}$ olefins is not particularly limited, and the olefins are selected from the group consisting of ethylene, 1-propene, 2-propene, 1-butene, 2-butene, 1-pentene, 2-pentene, 3-pentene, 1-hexene, 2-hexene, 3-hexene, 1-heptane, 2-heptane, 3-heptane, 4-heptane, 1-octene, 2-octene, 3-octene, 4-octene, 1-nonene, 2-nonene, 3-nonene, 4-nonene, 1-decene, 2-decene, 3-decene, 4-decene, 5-decene, 1-undecene, 2-undecene, 3-undecene, 4-undecene, 5-undecene, 1-dodecene, 2-dodecene, 3-dodecene, 4-dodecene, 5-dodecene, 6-dodecene, 1-tridecene, 2-tridecene, 3-tridecene, 4-tridecene, 5-tridecene, 6-tridecene, 1-tetradecene, 2-tetradecene, 3-tetradecene, 4-tetradecene, 5-tetradecene, 6-tetradecene, 7-tetradecene, 1-pentadecene, 2-pentadecene, 3-pentadecene, 4-pentadecene, 5-pentadecene, 6-pentadecene, 7-pentadecene, 1-hexadecene, 2-hexadecene, 3-hexadecene, 4-hexadecene, 5-hexadecene, 6-hexadecene, 7-hexadecene, 8-hexadecene, 1-heptadecene, 2-heptadecene, 3-heptadecene, 4-heptadecene, 5-heptadecene, 6-heptadecene, 7-heptadecene, 8-heptadecene, 1-octadecene, 2-octadecene, 3-octadecene, 4-octadecene, 5-octadecene, 6-octadecene, 7-octadecene, 8-octadecene, 1-nonadecene, 1-eicosene, 9-heneicosene, 1-docosene, butadiene, and mixtures thereof.

In a further exemplary embodiment, the disclosure provides a pressure-sensitive adhesive composition comprising a (meth)acrylate polymer comprising interpolymerized monomers made from a mixture of olefins, wherein 80% to 100% by weight, or 95% to 100% by weight, of the mixture of olefins are biobased olefins, as determined using ASTM D6866-12.

In yet another exemplary embodiment, the disclosure provides a mixture of olefins made by a method comprising reacting a $C_2$-$C_{22}$ primary alcohol with an acid catalyst at a temperature of 150° C. to 190° C. Optionally, the olefins comprise a single unsaturation and are biobased, as determined using ASTM D6866-12. The primary alcohol is preferably selected from the group consisting of $C_2$ alcohols, $C_4$ alcohols, $C_6$ alcohols, $C_8$ alcohols, $C_{10}$ alcohols, $C_{12}$ alcohols, $C_{14}$ alcohols, $C_{16}$ alcohols, $C_{18}$ alcohols, $C_{20}$ alcohols, $C_{22}$ alcohols, and mixtures thereof. Similar to the methods described above, the acid catalyst may comprise a heterogeneous acid catalyst, for example a cation exchange resin. In at least certain embodiments, the acid catalyst comprises sulfonic acid functional groups.

In a still further exemplary embodiment, the disclosure provides a method of making a mixture of olefins comprising reacting a secondary alcohol with an acid catalyst at a temperature of 100° C. to 190° C. The secondary alcohol is a biobased alcohol, as determined using ASTM D6866-12. Preferably, the secondary alcohol is 2-octanol, derived from castor oil. The 2-octanol has a $^{14}$C/C ratio of $1.0 \times 10^{-14}$ or higher, or $1.0 \times 10^{-13}$ or higher, or $1.0 \times 10^{-12}$ or higher. For instance, the secondary alcohol may be selected from the group consisting of $C_8$ alcohols, $C_{12}$ alcohols, and mixtures thereof.

In an additional embodiment, the disclosure provides a method of making a mixture of olefins comprising reacting a $C_2$-$C_{22}$ primary alcohol with an acid catalyst at a temperature of 150° C. to 190° C. The reaction is performed in a continuous reactor at a constant weight hourly space velocity (WHSV) of 0.5 h$^{-1}$ ($1.4 \times 10^{-4}$ s$^{-1}$) to 10 h$^{-1}$, ($2.8 \times 10^{-3}$ s$^{-1}$), or 0.1 h$^{-1}$ ($2.8 \times 10^{-5}$ s$^{-1}$) to 3 h$^{-1}$ ($8.3 \times 10^{-4}$ s$^{-1}$), or 0.3 h$^{-1}$ ($8.3 \times 10^{-4}$ s$^{-1}$) to 1 h$^{-1}$ ($2.8 \times 10^{-4}$ s$^{-1}$), or 0.5 h$^{-1}$ ($1.4 \times 10^{-4}$ s$^{-1}$) to 1.5 h$^{-1}$ ($4.2 \times 10^{-4}$ s$^{-1}$), or 0.5 h$^{-1}$ ($1.4 \times 10^{-4}$ s$^{-1}$) to 2 h$^{-1}$ ($5.6 \times 10^{-4}$ s$^{-1}$), or 0.2 h$^{-1}$ ($5.6 \times 10^{-5}$ s$^{-1}$) to 0.7 h$^{-1}$ ($1.9 \times 10$ s$^{-1}$). The WHSV is a ratio of mass flow of the $C_2$-$C_{22}$ primary alcohol entering the system per hour to the mass of the acid catalyst.

The acid catalyst preferably comprises a heterogeneous acid catalyst and the temperature of the method typically comprises 160° C. to 190° C. Certain cation exchange resins are thermally stable at such elevated temperatures, and thus may be preferred materials for the acid catalyst. In certain embodiments, the acid catalyst comprises a sulfonic acid catalyst. The acid catalyst typically comprises 0.05% to 50% by weight of the total reactants, such as 0.5 to 10% by weight of the total reactants. Optionally, the primary alcohol is dissolved in a solvent prior to or upon reacting with the acid catalyst. In such embodiments the solvent is selected from the group consisting of alkanes, alcohols, and aromatics having a higher boiling point than the olefins, for instance and without limitation, hexane, heptane, toluene, xylenes and combinations thereof.

The mixture of olefins produced by the method comprises between 80% and 100% by weight, or between 95% and 100% by weight, biobased olefins, as determined using ASTM D6866-12. The primary alcohol generally comprises a $C_4$-$C_{22}$ alcohol, and it may be linear, branched, saturated, unsaturated, or various combinations of these structural types. The primary alcohol is preferably derived from at least one plant oil, for example and without limitation at least one plant oil selected from the group consisting of almond oil, castor oil, coconut oil, soybean oil, rapeseed oil, cottonseed oil, sunflower seed oil, groundnut oil, palm oil, palm kernel oil, sesame oil, linseed oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, and combinations thereof.

In one embodiment, the present disclosure provides a (meth)acrylate polymer, particularly a pressure-sensitive adhesive composition that includes a (meth)acrylate polymer, including interpolymerized monomers that include at least three structural isomers of a secondary alkyl(meth) acrylate of Formula (I), as shown above.

In one aspect, a (meth)acrylate polymer, particularly one used in a pressure-sensitive adhesive, includes the interpolymerized reaction product of: (a) at least three structural isomers of a secondary alkyl(meth)acrylate of Formula (I); optionally (b) a (meth)acrylic acid ester of a $C_2$-$C_{22}$ alkanol; optionally (c) an acid-functional, ethylenically unsaturated monomer; optionally (d) a non-acid-functional, ethylenically unsaturated polar monomer; optionally (e) a vinyl monomer; and optionally (f) a multifunctional (meth)acrylate.

In one embodiment, the present disclosure provides a (meth)acrylate polymer, particularly a pressure-sensitive adhesive composition that includes a (meth)acrylate polymer, including at least three structural isomers of a moiety of Formula (II):

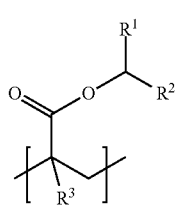

(II)

wherein $R^1$, $R^2$, and $R^3$ are as defined for Formula (I). In certain embodiments, a (meth)acrylate polymer includes at least three structural isomers of a moiety of Formula (II); and at least one moiety of a monomer selected from those listed as (b) through (f) above.

In certain embodiments of Formulas (I) and (II), $R^1$ and $R^2$ are each independently a $C_1$ to $C_{16}$ saturated linear alkyl and the sum of the number of carbons in $R^1$ and $R^2$ is 7 to 17.

In certain embodiments of Formulas (I) and (II), $R^1$ and $R^2$ are each independently a $C_1$ to $C_{14}$ saturated linear alkyl and the sum of the number of carbons in $R^1$ and $R^2$ is 11 to 15.

In certain embodiments of Formulas (I) and (II), $R^1$ and $R^2$ are each independently a $C_1$ to $C_6$ saturated linear alkyl and the sum of the number of carbons in $R^1$ and $R^2$ is 7 to 11.

In certain embodiments of Formulas (I) and (II), $R^1$ and $R^2$ are each independently a $C_1$ to $C_{16}$ saturated linear alkyl and the sum of the number of carbons in $R^1$ and $R^2$ is 9 to 17.

In one embodiment, the present disclosure provides a method of making a mixture of structural isomers of a secondary alkyl (meth)acrylate of Formula (I), as shown above.

The present disclosure also provides a mixture of structural isomers of a secondary alkyl(meth)acrylate of Formula (I), as shown above. A polymer made from this mixture is also provided.

Also provided is a method of making a mixture of structural isomers of a secondary alkyl(meth)acrylate of Formula (I), as shown above. The method involves reacting (meth)acrylic acid with an olefin having a single unsaturation, wherein the olefin has been pre-treated with an acid to give a mixture of olefin isomers.

A (meth)acrylate polymer (that is particularly suitable for use in a pressure-sensitive adhesive polymer) is provided that includes interpolymerized monomers that include: (a) at least three structural isomers of a secondary alkyl(meth) acrylate of Formula (I), as shown above; and (b) at least one monomer selected from: i) a (meth)acrylic acid ester of a $C_1$-$C_{22}$ alkanol; ii) an acid-functional, ethylenically unsaturated monomer; iii) a non-acid-functional, ethylenically unsaturated polar monomer; iv) a vinyl monomer; and v) a multifunctional (meth)acrylate. In certain embodiments, the 2-alkyl(meth)acrylate isomer of the three structural isomers used to prepare this polymer is less than 35 mole-% of the total mixture of secondary alkyl(meth)acrylate isomers.

The polymers, particularly the pressure-sensitive adhesive polymers, of the present disclosure may optionally be prepared from other monomers, crosslinkers, and additives. In particular, the pressure-sensitive adhesive may further include a tackifier. The pressure-sensitive adhesives of this disclosure will preferably provide a desired balance of tack, peel adhesion, and shear holding power, and further conform to the Dahlquist criterion for tack (storage modulus less than $3 \times 10^6$ dynes/cm$^2$ at room temperature and oscillation frequency of 1 Hz).

The (meth)acrylate polymers of the present disclosure are particularly useful in pressure-sensitive adhesives. Long linear alkyl chains (e.g., 1-octadecyl acrylate-$C_{18}$) can lead to crystalline groups within the polymer that will significantly reduce its degree of tack. If the crystalline temperature can be suppressed, longer chain alkyl acrylates can have a number of beneficial PSA properties over traditional $C_8$ acrylates such as reduced $T_g$ for broader use temperatures, lower storage modulus for quickly conforming and adhering to substrates, and lower polarity for adhering to low surface energy substrates to name a few. The branching pattern of the alkyl(meth)acrylate monomers of Formula (I) (or moieties of Formula (II)) allows the use of long alkyl chain structures while avoiding significant increases in crystalline temperature ($T_c$) that would decrease PSA performance. Furthermore, use of a mixture (e.g., blend) of structural isomers of the alkyl(meth)acrylate monomers of Formula (I) (or moieties of Formula (II)) has the added effect of depressing the crystalline temperature compared to traditional single structural isomer long chain linear or secondary alkyl acrylates. Depressing the $T_c$ of long chain alkyl acrylates has many advantages in PSA materials including a broader use temperature range, improved rheological behavior, and greater compatibility with a wide range of PSA additives. Preferably, a pressure-sensitive adhesive of the present disclosure has a $T_c$ of $\leq 0°$ C.

The compositions, particularly pressure-sensitive adhesive compositions, of this disclosure relate to the use of a mixture of structural isomers of secondary alkyl(meth)acrylate monomers, which form polymers with unique and improved properties over comparable, commonly used PSA (meth)acrylate polymers. The use of a mixture of structural isomers results in a depressed crystalline temperature ($T_c$) for polymers made therefrom, compared to polymers made using a single long alkyl chain (meth)acrylate. By decreasing the $T_c$, long chain alkyl(meth)acrylates can be formulated into PSAs with a number of beneficial characteristics, such as the ability to formulate with non-polar tackifiers.

Thus, the present disclosure provides a method for the production of alkyl acrylates and alkyl methacrylates based on the esterification of acrylic acid or methacrylic acid with a mixture of olefins in the presence of an acid catalyst (which is preferably used in a catalytic amount) as shown by example using 2-octene in Scheme II (in this scheme, R is H or $CH_3$).

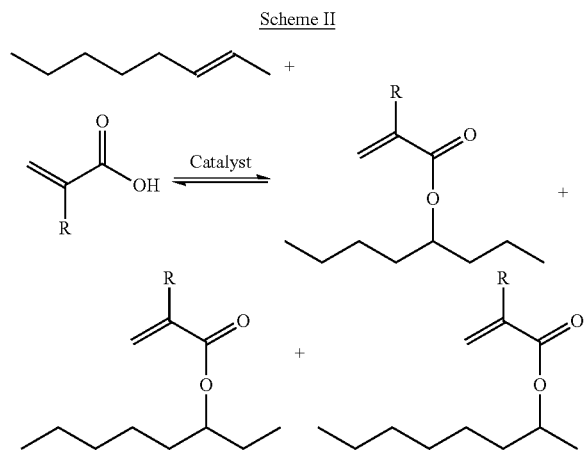

Scheme II

Embodiments of this method are very economical and provide high purity products. Once a typical reaction reaches equilibrium the yield can be increased by using an excess of either the acid or the olefin. The reagent used in excess, for example, can then be reclaimed and recycled.

In an embodiment of the present disclosure for making a mixture of structural isomers of a secondary alkyl(meth)acrylate of Formula (I) as described herein, the method involves reacting (meth)acrylic acid with a mixture of olefins in the presence of a acid catalyst.

Preferably, the esterification of acrylic acid or methacrylic acid with a mixture of olefins according to the present disclosure can provide product yields (conversions) of at least 30%, at least 40%, at least 50%, or at least 60%. Significantly, because fewer undesired by-products are formed using the method of the present disclosure, unreacted starting materials can be reclaimed and recycled. Thus, even though these reactions don't go to completion because they reach an equilibrium mixture of reactants and products, if yields were calculated based on reactants consumed, reaction yields could be considered close to quantitative.

An advantage of embodiments of the present disclosure is that due to isomerization of the olefin during dehydration of a biobased alcohol, a mixture of olefin isomers is produced from a single alcohol, and tends towards forming the internal isomers. Accordingly, separate isomerization process steps are typically not required to obtain a mixture of olefin isomers.

An olefin may also further be isomerized to a mixture of olefins prior to addition of (meth)acrylic acid by reaction with the acid catalyst. Typically, the catalyst used for this pre-isomerization process is the same as that used for the reaction between the olefin and (meth)acrylic acid. The temperature of the pre-isomerization process is typically 70-100° C. Often, an equal distribution of the internal isomers is obtained with only a small amount of the alpha-olefin. With this pre-isomerization process, the resultant secondary (meth)acrylate products are more equally distributed resulting in less of the 2-alkyl(meth)acrylate isomer and more internal (meth)acrylate isomers (such as 3-, 4-, and 5-alkyl(meth)acrylates). Generally, as the percentage of the 2-isomer decreases in the various secondary (meth)acrylate blends, the $T_c$ and $T_m$ of the resulting polymer decreases accordingly.

Thus, the present disclosure provides a mixture of structural isomers of a secondary alkyl(meth)acrylate of Formula (I) as described herein. Such a mixture can provide a novel polymer comprising biobased material. For example, isomers of Formula (I) can be interpolymerized with at least one monomer selected from: i) a (meth)acrylic acid ester of a $C_1$-$C_{32}$ alkanol; ii) an acid-functional, ethylenically unsaturated monomer; iii) a non-acid-functional, ethylenically unsaturated polar monomer; iv) a vinyl monomer; and v) a multifunctional (meth)acrylate.

In the esterification of (meth)acrylic acid with a mixture of olefins, the amount of olefin and (meth)acrylic acid can vary as desired. As mentioned above, one reagent can be used in excess relative to the other to decrease the time of the reaction and increase the yield.

The esterification of acrylic acid or methacrylic acid with a biobased olefin or mixture of olefins according to the present disclosure is typically carried out neat, i.e., in the absence of solvent. If desired, however, solvents such as alkanes, alcohols, and aromatics (e.g., hexane, heptane, toluene, and xylenes) can be used.

In certain embodiments, the present disclosure provides a continuous process for the esterification of acrylic acid or methacrylic acid with a biobased olefin or a mixture of olefin isomers. Preferably, the continuous process uses a fixed-bed heterogeneous catalyst flow-through system. In a continuous process of these embodiments, a reactor, typically a tubular reactor, having an inlet for reactants and an outlet for products is charged with a fixed bed of solid acid catalyst and used to perform the desired chemical transformation(s). This reactor configuration, often described as a "packed-bed reactor," can be advantageous when compared to homogeneously catalyzed batch reactions, similar to the advantages discussed above with respect to continuous stirred tank reactors. As an alternative to using a packed-bed reactor configuration, other well known continuous reactor configurations may be employed such as "continuous stirred tank" reactors or "reactive distillation" reactors.

A wide variety of commercially available solid (typically, resin) acid catalysts may be used with a packed-bed reactor, for example, in a continuous process. In particular, solid acid (heterogeneous) catalysts may be advantageously used in performing the desired chemical transformation(s) disclosed herein including, but not limited to, high fluorine content aliphatic sulfonic acids (e.g., those available under the trade name NAFION) and sulfonated styrene divinylbenzene copolymers (e.g., those available under the trade name AMBERLYST). Selection of a suitable solid acid catalyst material is typically determined by cost, rate of reaction, and selectivity to desired products.

In one exemplary continuous process, biobased olefin, and acid reactants (as described herein) are mixed prior to entering or upon entering the reaction zone, defined to be the volume in the tubular reactor occupied by the heterogeneous catalyst material. Time required to perform the desired reaction can vary, primarily due to catalyst type and temperature. Reactant residence time may be controlled, for example, by adjusting the total reactant feed rate to the reactor. Reactant residence time is typically held constant at values of at least 1 minute, and often at least 5 minutes. Reactant residence time is typically held constant at values of no greater than 120 minutes, and often no greater than 20 minutes. Reaction temperatures may be controlled with resistively heated insulating tape or by circulating heating oil from a temperature controlled bath, or other conventional methods. Typical reaction temperatures are at least 40° C., and often at least 50° C. Typical reaction temperatures are no greater than 150° C., and often at least 90° C. These temperatures produce single pass yields and selectivities in reasonable amounts of time. Reaction pressures may be controlled by a back pressure regulator placed at the outlet of the reactor unit, or other conventional methods. Typically, reaction pressures are no greater than 5 MPa, and often no greater than 1 MPa. These pressures will typically keep reagents in the liquid phase while reducing the need for specialized equipment that can withstand elevated pressures.

Whether in a continuous or batch process, after the reaction of the olefin(s) and (meth)acrylic acid, the crude secondary (meth)acrylate product is typically purified. When an excess of olefin relative to (meth)acrylic acid is used in the reaction, the product is typically isolated by distillation to separate unreacted olefin and the secondary (meth)acrylate product. Alternatively, the crude reaction mixture can be first extracted with a basic or a neutral aqueous solution (e.g., aqueous sodium bicarbonate) to remove any residual (meth)acrylic acid followed by distillation to isolate the secondary (meth)acrylate product.

During the reaction and subsequent purification procedures, a polymerization inhibitor is typically added. Suitable examples include, but are not limited to: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 4-aminophenol; 2-aminophenol; 2-N, N-dimethylaminophenol; catechol monobutylether; 2,3 dihydroxyacetophenone; pyrogallo1-1,2-dimethylether; t-butyl catechol; di-tertbutylnitroxide; di-tert-amylnitroxide; 2,2,6,6-tetramethylpiperidinyloxy; 4-hydroxy-2,2,6,6-tetramethyl-piperidinyloxy; 4-oxo-2,2,6,6-tetramethyl-piperidinyloxy; copper dimethyldithiocarbamate; copper salicylate; methylene blue; iron; phenothiazine; 3-oxophenothiazine; and 1,4-benzenediamine. The inhibitor or combination of inhibitors is typically added from 0.01 wt. % to 5.0 wt. %, based on the total volume of the reaction mixture.

The polymer (preferably pressure-sensitive adhesive polymer) of the present disclosure may include other monomers to modify the physical properties of the polymer produced by polymerization of at least three structural isomers of an alkyl(meth)acrylate monomer of Formula (I). Additionally, the polymers, particularly the pressure-sensitive adhesive polymers, of the present disclosure may include crosslinkers, and other additives, such as tackifiers or plasticizers. In one aspect, the polymer (preferably pressure-sensitive adhesive polymer) includes the interpolymerized reaction product of: (a) at least three structural isomers of a secondary alkyl (meth)acrylate of Formula (I) comprising biobased material; optionally (b) a (meth)acrylic acid ester of a $C_1$-$C_{32}$ alkanol; optionally (c) an acid-functional, ethylenically unsaturated monomer; optionally (d) a non-acid-functional, ethylenically unsaturated polar monomer; optionally (e) a vinyl monomer; and optionally (f) a multifunctional (meth)acrylate. In certain embodiments, the interpolymerized monomers include at least one monomer selected from a (meth)acrylic acid ester of a $C_1$-$C_{32}$ alkanol, an acid-functional, ethylenically unsaturated monomer, a non-acid-functional, ethylenically unsaturated polar monomer, and a mixture thereof, and optionally one or more of the vinyl monomer and multifunctional (meth)acrylate. In certain other embodiments, the interpolymerized monomers include an acid-functional, ethylenically unsaturated monomer.

The compositions used to form the polymers, particularly the pressure-sensitive adhesive polymers, of the present disclosure may include only a polymerized alkyl(meth) acrylate monomer of Formula (I) comprising at least three structural isomers, which may sometimes be referred to as a homopolymer. In many preferred embodiments, the composition includes 20 to 99.5, and in more preferred embodiments 50 to 95, parts by weight of a mixture of isomers of a secondary alkyl(meth)acrylate of Formula (I), relative to 100 parts total monomer.

The polymers, particularly the pressure-sensitive adhesive polymers, of the present disclosure may further comprise interpolymerized monomer units of a $C_1$-$C_{32}$ (meth) acrylate ester monomer (i.e., (meth)acrylic acid ester of a $C_1$-$C_{32}$ alkanol). These are typically distinct monomers from the compounds of Formula (I). In some embodiments, these are $C_1$-$C_{24}$, $C_1$-$C_{18}$, or $C_1$-$C_{12}$ (meth)acrylate ester monomers. Examples of monomers suitable for use as the $C_1$-$C_{32}$ (meth)acrylate ester monomer include an ester of either acrylic acid or methacrylic acid with a non-tertiary alkanol such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomers are suitable.

In some embodiments it is desirable for the $C_1$-$C_{32}$ (meth)acrylate ester monomer to include a high $T_g$ monomer, having a homopolymer $T_g$ of at least 25° C., and preferably at least 50° C. Examples of suitable high $T_g$ monomers useful in the present disclosure include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5-trimethylcyclohexyl acrylate, cyclohexyl acrylate, propyl methacrylate, and combinations thereof.

If present, a $C_1$-$C_{32}$ (meth)acrylate ester monomer is present in an amount of up to 80 parts by weight, and preferably up to 45 parts by weight, based on 100 parts total monomers. If present, a $C_1$-$C_{32}$ (meth)acrylate ester monomer is present in an amount of at least 1 part by weight, and preferably at least 5 parts by weight, based on 100 parts total monomers. In certain embodiments, a $C_1$-$C_{32}$ (meth)acrylate ester monomer is present in an amount of 1 part to 45 parts, and in other embodiments 5 parts to 45 parts, by weight, based on 100 parts total monomers. When a high $T_g$ monomer is included, the copolymer may include up to 50 parts by weight, preferably, 10 to 20 parts by weight, relative to 100 parts by weight of $C_1$-$C_{32}$ (meth)acrylate ester monomer component.

The composition used to form the polymers, particularly the pressure-sensitive adhesive polymers, of the present disclosure may further include an acid-functional monomer, wherein the acid-functional group may be an acid per se, such as a carboxylic acid, or a portion may be salt thereof, such as an alkali metal carboxylate. Useful acid-functional monomers include, but are not limited to, those selected from an ethylenically unsaturated carboxylic acid, ethylenically unsaturated sulfonic acid, ethylenically unsaturated phosphonic acid, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, an acid-functional monomer is generally selected from ethylenically unsaturated carboxylic acids (i.e., (meth)acrylic acids). When even stronger acids are desired, acidic monomers can include the ethylenically unsaturated sulfonic acids and ethylenically unsaturated phosphonic acids.

If present, an acid-functional, ethylenically unsaturated monomer is present in an amount of up 20 parts by weight, preferably up to 15 parts by weight, and more preferably up to 10 parts by weight, based on 100 parts total monomers. If present, an acid-functional, ethylenically unsaturated monomer is present in an amount of at least 0.5 parts by weight, preferably at least 1.0 part by weight, and more preferably at least 1.5 parts by weight, based on 100 parts total monomers. In certain embodiments, an acid-functional, ethylenically unsaturated monomer is present in an amount of 0.5 parts to 20 parts by weight, and in other embodiments 1.0 part to 15 parts by weight, and in still other embodiments, 1.5 parts to 10 parts by weight, based on 100 parts total monomers.

The composition used to form the polymers, particularly the pressure-sensitive adhesive polymers, of the present disclosure may further include a polar monomer. A polar monomer useful in preparing the polymer of the present disclosure is both somewhat oil soluble and water soluble. As used herein, the term "polar monomer" is exclusive of acid-functionality and is referred to as a "non-acid-functional, ethylenically unsaturated polar monomer."

Representative examples of suitable such polar monomers include, but are not limited to, 2-hydroxyethyl(meth)acrylate; 4-hydroxybutyl(meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; a poly(alkoxyalkyl)(meth)acrylate including 2-(2-ethoxyethoxy)ethyl(meth)acrylate, 2-ethoxyethyl(meth)acrylate, 2-methoxyethoxyethyl(meth) acrylate, 2-methoxyethyl methacrylate, and a polyethylene glycol mono(meth)acrylate; an alkyl vinyl ether, including vinyl methyl ether; and mixtures thereof. Preferred polar monomers include those selected from the group consisting of 2-hydroxyethyl(meth)acrylate, N-vinylpyrrolidinone, and mixtures thereof.

If present, a non-acid-functional, ethylenically unsaturated polar monomer is present in an amount of up 10 parts by weight, based on 100 parts total monomers. If present, a non-acid-functional, ethylenically unsaturated polar monomer is present in an amount of at least 0.5 parts by weight, based on 100 parts total monomers.

The composition used to form the polymers, particularly the pressure-sensitive adhesive polymers, of the present disclosure may further include one or more other vinyl monomers. When used, vinyl monomers useful in the (meth)acrylate polymer include a vinyl ester (e.g., vinyl acetate and vinyl propionate), styrene, substituted styrene (e.g., α-methyl styrene), vinyl halide, and mixtures thereof. As used herein vinyl monomers are exclusive of acid-functional monomers, acrylate ester monomers, and polar monomers.

If present, a vinyl monomer is present in an amount of up 5 parts by weight, based on 100 parts total monomers. If present, a vinyl monomer is present in an amount of at least 1.0 part by weight, based on 100 parts total monomers.

There are several crosslinking mechanisms for acrylic polymers (particularly, adhesives) including free-radical copolymerization of multifunctional, ethylenically unsaturated groups with the other monomers, and covalent or ionic crosslinking through the functional monomers, such as acrylic acid. A suitable covalent crosslinker includes bis-aziridines, for instance 1,1'-isophthaloylbis(2-methylaziridine). Another method is the use of UV crosslinkers, such as copolymerizable benzophenones or post-added photocrosslinkers, such as multifunctional benzophenones and triazines. In the past, a variety of different materials have been used as crosslinking agents, e.g., polyfunctional acrylates, acetophenones, benzophenones, and triazines. Crosslinking may also be achieved using high energy electromagnetic radiation such as gamma or e-beam radiation. In this case, no additional crosslinker may be required. One or more of these mechanisms can be used with the polymers described herein.

In order to increase cohesive strength of the coated (particularly, adhesive) composition, a multifunctional (meth)acrylate may be incorporated into the blend of polymerizable monomers. A multifunctional (meth)acrylate is particularly useful for emulsion or syrup polymerization. Examples of a useful multifunctional (meth)acrylate include, but are not limited to, a di(meth)acrylate, tri(meth)acrylate, and tetra(meth)acrylate, such as 1,6-hexanediol di(meth)acrylate, a poly(ethylene glycol) di(meth)acrylate, polybutadiene di(meth)acrylate, a polyurethane di(meth)acrylate, propoxylated glycerin tri(meth)acrylate, and mixtures thereof.

If present, a multifunctional (meth)acrylate monomer is present in an amount of up 5 parts by weight, and preferably up to 1.0 parts by weight, based on 100 parts total monomers. If present, a multifunctional (meth)acrylate monomer is present in an amount of at least 0.01 parts by weight, and preferably at least 0.05 parts by weight, based on 100 parts total monomers. In certain embodiments, a multifunctional (meth)acrylate monomer is present in an amount of 0.01 parts to 5 parts by weight, and in other embodiments 0.05 parts to 1.0 parts by weight, based on 100 parts total monomers.

In some embodiments, the interpolymerized monomers can include:

a) up to 100, preferably 20 to 99.5, more preferably 50 to 95, parts by weight of a component comprising at least three structural isomers of a secondary alkyl(meth)acrylate of Formula (I) comprising biobased material;

b) 0 to 80, preferably 1 to 45, more preferably 5 to 45, parts by weight of a (meth)acrylic acid ester of a $C_1$-$C_{32}$ alkanol;

c) 0.5 to 20, preferably 1.0 to 15, more preferably 1.5 to 10, parts by weight of an acid-functional, ethylenically unsaturated monomer;

d) 0 to 10, preferably 0.5 to 20, parts by weight of a non-acid-functional, ethylenically unsaturated polar monomer; and e) 0 to 5, preferably 1 to 5 parts by weight of a vinyl monomer.

The polymers, particularly pressure-sensitive adhesive polymers, disclosed herein may be prepared by a variety of conventional free radical polymerization methods, including solution, radiation, bulk, dispersion, emulsion, and suspension processes. The monomer mixture may comprise a polymerization initiator, especially a thermal initiator or a photoinitiator of a type and in an amount effective to polymerize the monomers, as described below. For optical applications, solution, UV, and bulk processes are preferred. Other processes may introduce birefringence or foreign materials that may affect optic properties. The resulting adhesive copolymers of the present disclosure may be random or block copolymers.

The polymers may be prepared via suspension polymerizations as disclosed in U.S. Pat. No. 3,691,140 (Silver); U.S. Pat. No. 4,166,152 (Baker et al.); U.S. Pat. No.4,636,432 (Shibano et al); U.S. Pat. No. 4,656,218 (Kinoshita); and U.S. Pat. No. 5,045,569 (Delgado).

Water-soluble and oil-soluble initiators useful in preparing the (meth)acrylate polymers of the present disclosure are initiators that, on exposure to heat, generate free-radicals which initiate (co)polymerization of the monomer mixture. Suitable water-soluble initiators include, but are not limited to, those selected from the group consisting of potassium persulfate, ammonium persulfate, sodium persulfate, and mixtures thereof; an oxidation-reduction initiator such as the reaction product of an above-mentioned persulfate and a reducing agent such as those selected from the group consisting of sodium metabisulfite and sodium bisulfite; and 4,4'-azobis(4-cyanopentanoic acid) and its soluble salts (e.g., sodium, potassium). Suitable oil-soluble initiators include, but are not limited to, those selected from the group consisting of an azo compound such as VAZO 64 (2,2'-azobis(isobutyronitrile)) and VAZO 52 (2,2'-azobis(2,4-dimethylpentanenitrile)) (both available from E.I. du Pont de Nemours Co.), peroxides such as benzoyl peroxide and lauroyl peroxide, and mixtures thereof. When used, initiators may be included in an amount up to 1 parts by weight, preferably from 0.05 to 1 parts by weight, more preferably 0.1 to 0.5 parts by weight, relative to 100 parts by weight of total monomer.

The polymerizable mixture may optionally further comprise chain transfer agents to control the molecular weight of the resultant polymer. Examples of useful chain transfer agents include, but are not limited to, those selected from the group consisting of carbon tetrabromide, alcohols, mercaptans, and mixtures thereof. When present, the preferred chain transfer agents are isooctylthioglycolate and carbon tetrabromide. If used, the polymerizable mixture may include up to 0.5 parts by weight of a chain transfer agent, typically 0.01 parts by weight to 0.5 parts by weight, and preferably 0.05 parts by weight to 0.2 parts by weight, relative to 100 parts by weight of the total monomer.

A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of 40° C. to 100° C. until the reaction is completed, typically in 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and ethylene glycol alkyl ether. Those solvents can be used alone or as mixtures thereof.

In a typical photopolymerization method, a monomer mixture may be irradiated with ultraviolet (UV) rays in the presence of a photopolymerization initiator (i.e., photoinitiators). Preferred photoinitiators are those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 651, 184 and 2959.

Solventless polymerization methods may also be utilized to prepare the polymers, such as the continuous free radical polymerization method described in U.S. Pat. No. 4,619,979 (Kotnour et al.) and U.S. Pat. No. 4,843,134 (Kotnour et al.), the essentially adiabatic polymerization methods using a batch reactor described in U.S. Pat. No. 5,637,646 (Ellis), and the methods described for polymerizing packaged pre-adhesive compositions described in U.S. Pat. No. 5,804,610 (Hamer et al.).

The compositions of the present disclosure, particularly the pressure-sensitive adhesives, may also contain one or more conventional additives. Preferred additives include tackifiers, plasticizers, dyes, antioxidants, and UV stabilizers. Such additives can be used if they do not affect the superior properties of the pressure-sensitive adhesives, for example.

Conventional (meth)acrylic-based adhesives do not adhere well to certain substrates, such as certain types of automotive paints and low energy olefinic surfaces. Efforts have been made to improve the adhesion of (meth)acrylic-based adhesives, i.e., develop more aggressive tack, to these types of surfaces; tackifying the base acrylic polymer is commonly practiced. The tackifier is generally selected to be miscible with the (meth)acrylate polymer used to form the PSA. Suitable tackifying resins include rosins and their derivatives (e.g., rosin esters); polyterpenes and aromatic-modified polyterpene resins; coumarone-indene resins; and hydrocarbon resins such as alpha pinene-based resins, beta pinene-based resins, limonene-based resins, aliphatic hydrocarbon-based resins, aromatic-modified hydrocarbon-based resins, aromatic hydrocarbon resins, and dicyclopentadiene-based resins. In certain embodiments, the tackifier is a terpene resin, a hydrocarbon resin, a rosin resin, a petroleum resin, or combination thereof. Combinations of various tackifiers can be used if desired. These tackifying resins, if desired, can be hydrogenated to lower their color contribution to the pressure-sensitive adhesive layer.

Various types of tackifiers include phenol modified terpenes and rosin esters such as glycerol esters of rosin and pentaerythritol esters of rosin that are available under the trade names NUROZ, NUTAC (Newport Industries), PERMALYN, STAYBELITE, FORAL (Eastman). Also available are hydrocarbon resin tackifiers that typically come from $C_5$ and $C_9$ monomers by products of naphtha cracking and are available under the trade names PICCOTAC, EASTOTAC, REGALREZ, REGALITE (Eastman), ARKON (Arakawa), NORSOLENE, WINGTACK (Cray Valley), NEVTAC LX (Neville Chemical Co.), HIKOTACK, HIKOREZ (Kolon Chemical), NOVARES (Ruetgers Nev.), QUINTONE (Zeon), ESCOREZ (Exxon Mobile Chemical), NURES, and H-REZ (Newport Industries).

Due to the high solubility parameter of most conventional (meth)acrylic-based polymers used in pressure-sensitive adhesives and the presence of specific potential interactions between these polymeric materials and many tackifiers, a limited selection of tackifiers is available to the formulator. As a class, hydrocarbon-based tackifiers, and especially hydrogenated hydrocarbon resins, are typically unsuitable for use in polar (meth)acrylic-based adhesives formulations due to their nonpolar character.

Rosin acid based tackifiers and selected phenol-modified terpene and alpha-pinene based resins perform well in a variety of conventional (meth)acrylic-based pressure-sensitive adhesives. However, some problems are still associated with the use of this limited range of tackifiers in such (meth)acrylic-based adhesives. Tackified (meth)acrylic-based pressure-sensitive adhesive formulations are often discolored or yellow. The yellow appearance of these tackified (meth)acrylic-based pressure-sensitive adhesives is a direct result of the distinct yellow tinge inherent in many of these tackifiers. Upon aging and exposure to light, this discoloration can become even more pronounced, even with lighter colored grades of resin. (Meth)acrylic-based adhesives without tackifiers typically have excellent aging properties.

Conventional tackified (meth)acrylic-based pressure-sensitive adhesives can also appear cloudy, demonstrating a loss in the characteristic transparency found in many conventional acrylate pressure-sensitive adhesive compositions. The cloudiness is an indication of limited or incomplete compatibility of the tackifier and the (meth)acrylic-based polymers. The reduced compatibility can lead to a degradation of adhesive properties on aging, as evidenced by a loss of tack or reduced peel adhesion. In some cases, the addition of a tackifier to an adhesive composition having (meth)acrylic-based monomers, polymers, oligomers, and any mixture thereof, can be clear and appear to be compatible. However, after removing the solvent, curing the adhesive, or on aging, the adhesive can become cloudy, indicating some incompatibility between the tackifier and (meth)acrylic-based polymer.

In addition to these losses in clarity and stability of tackified (meth)acrylic-based adhesives, other deleterious effects can be observed when tackifiers are present during bulk acrylic polymerization reactions. Depending on the structure of the tackifier, undesirable effects of adding a tackifier include the inhibition or retardation of the polymerization reaction and/or the alteration of the final polymer structure if the tackifier acts as a chain-transfer or chain-terminating agent. Such effects can adversely influence the performance and stability of acrylates polymerized in the presence of these tackifiers. Chain termination can also result in undesirably high residual volatile materials.

In many embodiments, the present disclosure may provide tackified PSA compositions that overcome problems noted in the art. The tackifier is preferably selected from a material that is essentially free of any ethylenically or acetylenically unsaturated bonds. In certain embodiments a tackifier selected from a hydrogenated terpene resin, a hydrogenated rosin resin, an esterified rosin resin, an aliphatic petroleum resin, an aromatic petroleum resin, an alicyclic petroleum resin obtained by hydrogenating aromatic petroleum resins, and combinations thereof. Preferably, the tackifier used is selected from hydrogenated $C_9$ petroleum resins such as but not limited to REGALREZ tackifiers (Eastman) or ARKON (Arakawa) tackifiers. Such "hydrophobic tackifiers" may be used in amounts of up to 150 parts, preferably 20 to 150 parts, more preferably 50 parts to 100 parts, of said tackifier, relative to 100 parts of said (meth)acrylate polymer.

The polymer compositions, particularly adhesives, of the present disclosure may be coated upon a variety of flexible and inflexible backing materials using, for example, conventional coating techniques to produce adhesive-coated materials. Flexible substrates are defined herein as any material that is conventionally utilized as a tape backing or may be of any other flexible material. Examples include, but are not limited to, plastic films such as polypropylene, polyethylene, polyvinyl chloride, polyester (polyethylene terephthalate), other polyesters (such as polyethylene naphthalate), polycarbonate, polymethyl(meth)acrylate (PMMA), cellulose acetate, cellulose triacetate, and ethyl cellulose. Foam backings may be used. Examples of inflexible substrates include, but are not limited to, metal, metallized polymeric film, indium tin oxide coated glass and polyester, PMMA plate, polycarbonate plate, glass, or ceramic sheet material. The adhesive-coated sheet materials may take the form of any article conventionally known to be utilized with adhesive compositions such as labels, tapes, signs, covers, marking indices, display components, touch panels, and the like. Flexible backing materials having microreplicated surfaces are also contemplated.

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating knife coating, and die coating. These various methods of coating allow the compositions to be placed on the substrate at variable thicknesses thus allowing a wider range of use of the compositions. Coating thicknesses may vary, but coating thicknesses of 2-500 microns (dry thickness), preferably 25 to 250 microns, are contemplated.

The substrate is selected depending on the particular application in which it is to be used. For example, the adhesive can be applied to sheeting products (e.g., decorative graphics and reflective products), label stock, and tape backings. Additionally, the adhesive may be applied directly onto a substrate such as an automotive panel, or a glass window so that another substrate or object can be attached to the panel or window.

The adhesive can also be provided in the form of a pressure-sensitive adhesive transfer tape in which at least one layer of the adhesive is disposed on a release liner for application to a permanent substrate at a later time. The adhesive can also be provided as a single coated or double coated tape in which the adhesive is disposed on a permanent backing. Backings can be made from plastics (e.g., polypropylene, including biaxially oriented polypropylene, vinyl, polyethylene, polyester such as polyethylene terephthalate), nonwovens (e.g., papers, cloths, nonwoven scrims), metal foils, foams (e.g., polyacrylic, polyethylene, polyurethane, neoprene), and the like. Foams are commercially available from various suppliers such as 3M Co., Voltek, Sekisui, and others. The foam may be formed as a coextruded sheet with the adhesive on one or both sides of the foam, or the adhesive may be laminated to it. When the adhesive is laminated to a foam, it may be desirable to treat the surface to improve the adhesion of the adhesive to the foam or to any of the other types of backings. Such treatments are typically selected based on the nature of the materials of the adhesive and of the foam or backing and include primers and surface modifications (e.g., corona treatment, surface abrasion). Additional tape constructions include those described in U.S. Pat. No. 5,602,221 (Bennett et al.).

For a single-sided tape, the side of the backing surface opposite that where the adhesive is disposed is typically coated with a suitable release material. Release materials are known and include materials such as, for example, silicone, polyethylene, polycarbamate, polyacrylics, and the like. For double coated tapes, another layer of adhesive is disposed on the backing surface opposite that where the adhesive of the disclosure is disposed. The other layer of adhesive can be different from the adhesive of the disclosure, e.g., a conventional (meth)acrylic ester PSA, or it can be the same adhesive as the disclosure, with the same or a different formulation. Double coated tapes are typically carried on a release liner.

Exemplary Embodiments

1. A method of making a mixture of structural isomers of a secondary alkyl (meth)acrylate of Formula (I):

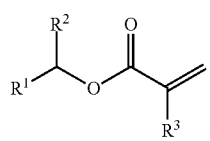

(I)

wherein:
R$^1$ and R$^2$ are each independently a C$_1$ to C$_{20}$ saturated linear alkyl group; the sum of the number of carbons in R$^1$ and R$^2$ is 2 to 21; and R$^3$ is H or CH$_3$.

wherein the method comprises:
dehydrating a biobased C$_2$-C$_{22}$ alcohol with a first acid catalyst using a continuous process, thereby forming a mixture of olefins; and
reacting (meth)acrylic acid with at least some of the mixture of olefins in the presence of a second acid catalyst.

2. The method of embodiment 1, wherein the C$_2$-C$_{22}$ alcohol is selected from the group consisting of C$_2$ alcohols, C$_3$ alcohols, C$_4$ alcohols, C$_5$ alcohols, C$_6$ alcohols, C$_7$ alcohols, C$_8$ alcohols, C$_9$ alcohols, C$_{10}$ alcohols, C$_{11}$ alcohols, C$_{12}$ alcohols, C$_{13}$ alcohols, C$_{14}$ alcohols, C$_{15}$ alcohols, C$_{16}$ alcohols, C$_{17}$ alcohols, C$_{18}$ alcohols, C$_{19}$ alcohols, C$_{20}$ alcohols, and mixtures thereof.

3. The method of embodiment 1 or embodiment 2 wherein the first acid catalyst comprises a heterogeneous acid catalyst.

4. The method of any one of embodiments 1 through 3 wherein the first acid catalyst comprises a cation exchange resin.

5. The method of any one of embodiments 1 through 4 wherein the mixture of olefins comprises between 80% and 100% by weight biobased olefins, as determined using ASTM D6866-12.

6. The method of any one of embodiments 1 through 5 wherein the mixture of olefins comprises between 95% and 100% by weight biobased olefins, as determined using ASTM D6866-12.

7. The method of any one of embodiments 1 through 6 wherein the dehydrating occurs at a temperature of 150° C. to 190° C.

8. The method of any one of embodiments 1 through 7 wherein the C$_2$-C$_{22}$ alcohol comprises a primary alcohol.

9. The method of any one of embodiments 1 through 7 wherein the C$_2$-C$_{22}$ alcohol comprises a secondary alcohol.

10. The method of any one of embodiments 1 through 7 wherein the C$_2$-C$_{22}$ alcohol comprises a tertiary alcohol.

11. The method of any one of embodiments 1 through 10 wherein the C$_2$-C$_{22}$ alcohol comprises a branched alcohol.

12. The method of any one of embodiments 1 through 10 wherein the C$_2$-C$_{22}$ alcohol comprises a linear alcohol.

13. The method of any one of embodiments 1 through 12 wherein the C$_2$-C$_{22}$ alcohol comprises a saturated alcohol.

14. The method of any one of embodiments 1 through 12 wherein the C$_2$-C$_{22}$ alcohol comprises an unsaturated alcohol.

15. The method of any one of embodiments 1 through 14 wherein the C$_2$-C$_{22}$ alcohol is derived from at least one plant oil.

16. The method of embodiment 15 wherein the at least one plant oil is selected from the group consisting of almond oil, castor oil, coconut oil, soybean oil, rapeseed oil, cottonseed oil, sunflower seed oil, groundnut oil, palm oil, palm kernel oil, sesame oil, linseed oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, and combinations thereof.

17. The method of any of embodiments 1 through 16 wherein the C$_2$-C$_{22}$ alcohol comprises a C$_8$ alcohol, a C$_{10}$ alcohol, or a C$_{12}$ alcohol.

18. The method of any one of embodiments 1 through 17 wherein the dehydrating is performed in a continuous reactor at a constant weight hourly space velocity (WHSV) of 0.5 h$^{-1}$ to 10 h$^{-1}$, wherein the WHSV is a ratio of mass flow of the C$_2$-C$_{22}$ alcohol entering the system per hour to the total mass of the first acid catalyst.

19. The method of any one of embodiments 1 through 18 wherein a combination of the mixture of olefins and water is produced at a rate of 0.5 g h$^{-1}$ to 10 g h$^{-1}$ per gram of the first acid catalyst.

20. The method of any one of embodiments 1 through 19 wherein a combination of the mixture of olefins and water is produced at a rate of 1 g h$^{-1}$ to 5 g h$^{-1}$ per gram of the first acid catalyst.

21. The method of any one of embodiments 1 through 20 wherein at least 75% of the C$_2$-C$_{22}$ alcohol by weight is recovered as a combination of the mixture of olefins and water.

22. The method of any one of embodiments 1 through 21 wherein at least 90% of the C$_2$-C$_{22}$ alcohol by weight is recovered as a combination of the mixture of olefins and water.

23. The method of any one of embodiments 1 through 22 wherein the mixture of olefins is continuously removed from the reactor.

24. The method of any one of embodiments 1 through 23 wherein the mixture of olefins is continuously removed from the reactor through a packed distillation column.

25. The method of any one of embodiments 1 through 24 further comprising adding water to the continuous reactor.

26. A mixture of C$_2$-C$_{22}$ olefins, wherein the olefins are biobased as determined using ASTM D6866-12.

27. The mixture of olefins of embodiment 26 wherein the olefins are selected from the group consisting of ethylene, 1-propene, 2-propene, 1-butene, 2-butene, 1-pentene, 2-pentene, 3-pentene, 1-hexene, 2-hexene, 3-hexene, 1-heptene, 2-heptene, 3-heptene, 4-heptene, 1-octene, 2-octene, 3-octene, 4-octene, 1-nonene, 2-nonene, 3-nonene, 4-nonene, 1-decene, 2-decene, 3-decene, 4-decene, 5-decene, 1-undecene, 2-undecene, 3-undecene, 4-undecene, 5-undecene, 1-dodecene, 2-dodecene, 3-dodecene, 4-dodecene, 5-dodecene, 6-dodecene, 1-tridecene, 2-tridecene, 3-tridecene, 4-tridecene, 5-tridecene, 6-tridecene, 1-tetradecene, 2-tetradecene, 3-tetradecene, 4-tetradecene, 5-tetradecene, 6-tetradecene, 7-tetradecene, 1-pentadecene, 2-pentadecene, 3-pentadecene, 4-pentadecene, 5-pentadecene, 6-pentadecene, 7-pentadecene, 1-hexadecene, 2-hexadecene, 3-hexadecene, 4-hexadecene, 5-hexadecene, 6-hexadecene, 7-hexadecene, 8-hexadecene, 1-heptadecene, 2-heptadecene, 3-heptadecene, 4-heptadecene, 5-heptadecene, 6-heptadecene, 7-heptadecene, 8-heptadecene, 1-octadecene, 2-octadecene, 3-octadecene, 4-octadecene, 5-octadecene, 6-octadecene, 7-octadecene, 8-octadecene, 1-nonadecene, 1-eicosene, 9-heneicosene, 1-docosene, and mixtures thereof.

28. The mixture of olefins of embodiment 26 or embodiment 27 wherein the olefins comprise a single unsaturation.

29. The mixture of olefins of embodiment 26 wherein the olefins comprise multiple unsaturations.

30. A pressure-sensitive adhesive composition comprising a (meth)acrylate polymer comprising interpolymerized monomers made from a mixture of olefins, wherein 80% to 100% by weight of the mixture of olefins are biobased olefins, as determined using ASTM D6866-12.

31. The pressure-sensitive adhesive composition of embodiment 30 wherein 95% to 100% by weight of the mixture of olefins are biobased olefins, as determined using ASTM D6866-12.

32. A mixture of olefins made by a method comprising reacting a $C_2$-$C_{22}$ primary alcohol with an acid catalyst at a temperature of 150° C. to 190° C.

33. The mixture of olefins of embodiment 32 wherein the olefins comprise a single unsaturation and wherein the olefins are biobased, as determined using ASTM D6866-12.

34. The mixture of olefins of embodiment 32 or embodiment 33 wherein the primary alcohol is selected from the group consisting of $C_2$ alcohols, $C_4$ alcohols, $C_6$ alcohols, $C_8$ alcohols, $C_{10}$ alcohols, $C_{12}$ alcohols, $C_{14}$ alcohols, $C_{16}$ alcohols, $C_{18}$ alcohols, and mixtures thereof.

35. The mixture of olefins of any one of embodiments 32 through 34 wherein the acid catalyst comprises a heterogeneous acid catalyst.

36. The mixture of olefins of any one of embodiments 32 through 35 wherein the acid catalyst comprises a cation exchange resin.

37. A method of making a mixture of olefins comprising reacting a secondary alcohol with an acid catalyst at a temperature of 100° C. to 190° C., wherein the secondary alcohol is a biobased alcohol, as determined using ASTM D6866-12.

38. The method of embodiment 37 wherein the secondary alcohol is 2-octanol derived from castor oil.

39. The method of embodiment 38 wherein the 2-octanol has a $^{14}C/C$ ratio of $1.0 \times 10^{-14}$ or higher.

40. The method of embodiment 37 wherein the secondary alcohol is selected from the group consisting of $C_8$ alcohols, $C_{12}$ alcohols, and mixtures thereof.

41. A method of making a mixture of olefins comprising reacting a $C_2$-$C_{22}$ primary alcohol with an acid catalyst at a temperature of 150° C. to 190° C., wherein the reaction is performed in a continuous reactor at a constant weight hourly space velocity (WHSV) of 0.5 h$^{-1}$ to 10 h$^{-1}$, wherein the WHSV is a ratio of mass flow of the $C_2$-$C_{22}$ primary alcohol entering the system per hour to the total mass of the acid catalyst.

42. The method of embodiment 41 wherein the acid catalyst comprises a heterogeneous acid catalyst.

43. The method of embodiment 41 or embodiment 42 wherein the acid catalyst comprises a cation exchange resin.

44. The method of any one of embodiments 41 through 43 wherein the temperature comprises 160° C. to 190° C.

45. The method of any one of embodiments 41 through 44 wherein the mixture of olefins comprises between 80% and 100% by weight biobased olefins, as determined using ASTM D6866-12.

46. The method of any one of embodiments 41 through 45 wherein the mixture of olefins comprises between 95% and 100% by weight biobased olefins, as determined using ASTM D6866-12.

47. The method of any one of embodiments 41 through 46 wherein the primary alcohol comprises a branched alcohol.

48. The method of any one of embodiments 41 through 47 wherein the primary alcohol comprises an unsaturated alcohol.

49. The method of any one of embodiments 41 through 48 wherein the primary alcohol comprises a $C_4$-$C_{22}$ alcohol.

50. The method of any one of embodiments 41 through 49 wherein the primary alcohol is derived from at least one plant oil.

51. The method of embodiment 50 wherein the at least one plant oil is selected from the group consisting of almond oil, castor oil, coconut oil, soybean oil, rapeseed oil, cottonseed oil, sunflower seed oil, groundnut oil, palm oil, palm kernel oil, sesame oil, linseed oil, maize oil, peanut oil, olive oil, hemp oil, corn oil, mustard oil, flaxseed oil, apricot oil, argan oil, avocado oil, ben oil, cashew oil, grape seed oil, hazelnut oil, neem oil, pumpkin seed oil, rice bran oil, walnut oil, safflower oil, copra oil, and combinations thereof.

52. The method of any one of embodiments 41 through 51 wherein a combination of the mixture of olefins and water is produced at a rate of 0.5 g h$^{-1}$ to 10 g h$^{-1}$ per gram of the acid catalyst.

53. The method of any one of embodiments 41 through 52 wherein a combination of the mixture of olefins and water is produced at a rate of 1 g h$^{-1}$ to 5 g h$^{-1}$ per gram of the acid catalyst.

54. The method of any one of embodiments 41 through 53 wherein at least 75% of the primary alcohol by weight is recovered as a combination of the mixture of olefins and water.

55. The method of any one of embodiments 41 through 54 wherein at least 90% of the primary alcohol by weight is recovered as a combination of the mixture of olefins and water.

56. The method of any one of embodiments 41 through 55 wherein the acid catalyst comprises 0.05% to 50% by weight of the total reactants.

57. The method of any one of embodiments 41 through 56 wherein the acid catalyst comprises 0.5 to 10% by weight of the total reactants.

58. The method of any one of embodiments 41 through 57 wherein the primary alcohol is dissolved in a solvent prior to or upon reacting with the acid catalyst.

59. The method of embodiment 58 wherein the solvent is selected from the group consisting of alkanes, alcohols, aromatics and combinations thereof.

60. The method of any one of embodiments 41 through 59 wherein the mixture of olefins is continuously removed from the reactor.

61. The method of any one of embodiments 41 through 60 wherein the mixture of olefins is continuously removed from the reactor through a packed distillation column.

62. The method of any one of embodiments 41 through 61 further comprising adding a diluent to the continuous reactor.

63. The method of any one of embodiments 41 through 62 further comprising adding water to the continuous reactor.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Summary of Materials

Unless otherwise noted, all parts, percentages, ratios, etc. in the Examples and the rest of the specification are by weight. Table 1 provides a role and a source for materials used in the Examples below:

TABLE 1

| Role | Material | Source |
| --- | --- | --- |
| Reactant | 1-Octanol (biobased) | Alfa Aesar, Ward Hill, MA |
| Reactant | 2-Octanol (biobased) | Alfa Aesar, Ward Hill, MA |
| Reactant | 1-Dodecanol (biobased) | Alfa Aesar, Ward Hill, MA |
| Reactant | Acrylic acid | BASF, Florham Park, NJ |
| Reactant | Methacrylic acid | Alfa Aesar, Ward Hill, MA |
| Catalyst | AMBERLYST 36 | Dow Chemical Company, Midland, MI |
| Catalyst | AMBERLYST 70 | Dow Chemical Company, Midland, MI |
| Catalyst Modifier | Deionized Water | — |

Test Method 1. Gel Permeation Chromatography

The characterization of the molecular weight of primer copolymer candidates was performed by conventional gel permeation chromatography (GPC). GPC instrumentation included a Waters 1515 HPLC pump, a Waters 717 Autosampler, a Waters 2487 UV detector, and a Waters 2410 refractive index detector, in addition to a liquid chromatograph equipped with two PLgel 5 micron Mixed D columns (Varian, Palo Alto, Calif.). Polymer samples were prepared by dissolution in tetrahydrofuran at a concentration of 0.5% (W/V) and filtered through a 0.2 micron polytetrafluoroethylene filter. Samples were injected and eluted at a rate of 1 milliliter per minute through the columns maintained at 35° C. The system was calibrated using polystyrene standards employing a linear least squares fit analysis. Molecular weight averages (Mw) for Example polymers were calculated against this calibration.

Test Method 2: 180° Peel Adhesion Strength Test

Peel adhesion is the force required to remove a coated flexible sheet material from a test panel measured at a specific angle and rate of removal. In these examples, the peel force is expressed in ounces per width of coated sheet (e.g. ounces/inch). For each test, 0.5 inch width of the adhesive coated sheet material approximately 6 inches long was cut from the coated adhesive. The adhesive strip was then applied to the clean face of a stainless steel test panel. A heavy rubber roller was used to apply the strip. The free end of the coated strip was doubled back so that the angle of removal was 180 degrees. The free end was attached to the horizontal arm of the adhesion tester scale. The stainless steel plate was then affixed to the platform of the instrument which is mechanized to move at a controlled rate (i.e., 12 inches/minute) away from the scale. The peel test was started soon after the adhesive was applied to the substrate without allowing for an induction time for adhesion to build. The scale reading in ounces was read during the test as an average of both the peak and minimum forces during the peel. Three peel tests were run for each sample and averaged to yield the peel adhesion value.

Test Method 3: High Temperature Shear Strength

Shear strength is measured in terms of the time required to pull a defined area of adhesive coated backing material from a stainless steel test panel under the stress of a constant or static load parallel to the test panel.

Shear tests were conducted using adhesive coated polyethylene terephthalate (PET) material with approximately a 2 mil (50.8 μm) thick adhesive coating. Cut adhesive strips were applied to a clean stainless steel panel such that a 0.5 inch by 1 inch portion of each strip was in firm contact with the panel and one end portion of each strip was free. The panel with adhesive strip was held in a rack such that the panel formed a 180 degree angle with the extended free end which was then tensioned by applying a 500 gram hanging weight. The rack was enclosed in a 70° C. oven and the time elapsed for each tape example to separate from the test panel was recorded as the shear strength in minutes. Two shear tests were performed for each sample adhesive and the shear strength averaged. Tests were discontinued if the sample was hanging for greater than 10,000 minutes and denoted with "+10,000" in the table.

Example 1

Octene from 1-Octanol

A 2 liter (L) Erlenmeyer flask was charged with 1200 grams (g) of 1-octanol derived from plant oil and 100 g AMBERLYST 70 catalyst material (a sulfonated styrene divinylbenzene copolymer). The flask was heated to approximately 180° C. and fed continuously with 1-octanol at a rate of 4.2 milliliters per minute (mL min$^{-1}$). During reaction, products water and octene were vaporized to a 1.5 inch (3.8 cm) inner diameter (I.D.) by 24 inch (61 cm) length fractionation column equipped with a condenser and reflux ratio control (i.e., reflux valve), which were held constant at 5° C. and a 1:1 ratio, respectively. After at least 1 hour of continuous operation, product was collected for analysis at a rate of 2.51 g h$^{-1}$ (g catalyst)$^{-1}$ (6.97×10$^{-4}$ g s$^{-1}$ (g catalyst)$^{-1}$) and was found to contain primarily a mixture of octene isomers and water. Water was then separated from the product mixture using a separatory funnel to yield octene product.

Example 2

Octene from 2-Octanol

A 3 L round-bottom flask was charged with 800 g of 2-octanol derived from plant oil and 100 g AMBERLYST 70 catalyst material (a sulfonated styrene divinylbenzene copolymer). The flask was heated to approximately 130° C. and fed continuously with 2-octanol at a rate of 6.66 mL min$^{-1}$. During reaction, product water and octene were vaporized to a 1.5 inch (3.8 cm) I.D. by 24 inch (61 cm) length fractionation column equipped with a condenser and a reflux ratio control (i.e., reflux valve), which were held constant at 5° C. and 1:1 ratio, respectively. After at least 1 hour of continuous operation, product was collected for analysis at a rate of 4.716 g h$^{-1}$ (g catalyst)$^{-1}$ (1.31×10$^{-3}$ g s$^{-1}$ (g catalyst)$^{-1}$) and was found to contain primarily a mixture of octene isomers and water. Water was then separated from the product mixture using a separatory funnel to yield octene product.

Example 3

Dodecene from 1-Dodecanol

A 3 L round-bottom flask was charged with 1000 g of 1-dodecanol derived from plant oil and 100 g AMBERLYST 70 catalyst material (a sulfonated styrene divinylbenzene copolymer). The flask was heated to approximately 170° C. and fed continuously with 1-dodecanol at a rate of 4.6 mL min$^{-1}$ During reaction, product water and dodecene were vaporized to a 1.5 inch (3.8 cm) I.D. by 24 inch (61 cm) length fractionation column equipped with a condenser and a reflux ratio control (i.e., reflux valve), which were held constant at 25° C. and 1:1 ratio, respectively. After at least 1 hour of continuous operation, product was collected for analysis at a rate of 2.18 g h$^{-1}$ (g catalyst)$^{-1}$ (6.05×10 g s$^{-1}$ (g catalyst)$^{-1}$) and was found to contain primarily a mixture of dodecene isomers and water. Water was then separated from the product mixture using a separatory funnel to yield dodecene product.

Example 4

Octyl Acrylate from Octene

A 0.622 inch (1.580 centimeter (cm)) I.D. by 30 inch (76 cm) length stainless steel reactor tube was charged with 100 g of AMBERLYST 36 Dry catalyst material (a sulfonated styrene divinylbenzene copolymer). A 1:2 molar ratio of pre-mixed octene:acrylic acid (i.e., octene produced using the method described in Example 1, and acrylic acid containing 200 ppm hydroquinone monomethyl ether (MEHQ) by weight) was fed to the reactor continuously at 1 mL min$^{-1}$ total flow rate (0.00340 moles per minute (mol min$^{-1}$) or 0.38163 g min$^{-1}$ of octene, 0.00680 mol min$^{-1}$ or 0.49003 g min$^{-1}$ of acrylic acid) and reactor pressure was maintained at approximately 50 psig (0.45 MPa). Reactor temperature was held constant at 60° C. Product was collected for analysis and purification.

The unpurified reaction mixture and found to contain primarily a mixture of acrylic acid, octene isomers, and octyl acrylate isomers. Yield of octyl acrylate was 49.1% by total weight, with an isomer distribution of 34.0%, 35.3%, and 30.7% of 2-octyl acrylate, 3-octyl acrylate, and 4-octyl acrylate, respectively. The crude product mixture was then purified by vacuum distillation. The first cut contained primarily octene, the second cut contained primarily acrylic acid, and the third cut contained primarily octyl acrylate.

Example 5

Octyl Methacrylate from Octene

A 0.622 inch (1.580 cm) I.D. by 30 inch (76 cm) length stainless steel reactor tube was charged with 100 g of AMBERLYST 36 Dry catalyst material (a sulfonated styrene divinylbenzene copolymer). A 1:2 molar ratio of pre-mixed octene:methacrylic acid (octene produced using the method described in Example 1, and methacrylic acid containing 200 ppm MEHQ by weight) was fed to the reactor continuously at 1 mL min$^{-1}$ total flow rate (0.00307 mol min$^{-1}$ or 0.34459 g min$^{-1}$ of octene, 0.00614 mol min$^{-1}$ or 0.52842 g min$^{-1}$ of methacrylic acid) and reactor pressure was maintained at approximately 50 psig (0.45 MPa). Reactor temperature was held constant at 60° C. Product was collected for analysis and purification.

The unpurified reaction mixture and found to contain primarily a mixture of methacrylic acid, octene isomers, and octyl methacrylate isomers. Yield of octyl methacrylate was 43.1% by total weight, with an isomer distribution of 42.0%, 31.5%, and 26.5% of 2-octyl methacrylate, 3-octyl methacrylate, and 4-octyl methacrylate, respectively. The crude product mixture was then purified by vacuum distillation. The first cut contained primarily octene, the second cut contained primarily methacrylic acid, and the third cut contained primarily octyl methacrylate.

Example 6

Dodecyl Acrylate from Dodecene

A 0.622 inch (1.580 cm) I.D. by 30 inch (76 cm) length stainless steel reactor tube was charged with 100 g of Amberlyst 36 Dry catalyst material (a sulfonated styrene divinylbenzene copolymer). A 1:2.5 molar ratio of pre-mixed dodecene:acrylic acid (dodecene produced using the method described in Example 3, acrylic acid containing 200 ppm MEHQ by weight) was fed to the reactor continuously at 1 mL min-1 total flow rate (0.00255 mol min-1 or 0.42906 g min-1 of dodecene, 0.00637 mol min-1 or 0.45921 g min-1 of acrylic acid) and reactor pressure was maintained at approximately 50 psig (0.45 MPa). Reactor temperature was held constant at 75° C. Product was collected for analysis and purification.

The unpurified reaction mixture and found to contain primarily a mixture of acrylic acid, dodecene isomers, and dodecyl acrylate isomers. Yield of dodecyl acrylate was 28.8% by total weight, with an isomer distribution of 17.8%, 19.1%, 18.2%, 16.4%, and 28.5% of 2-dodecyl acrylate, 3-dodecyl acrylate, 4-dodecyl acrylate, 5-dodecyl acrylate, and 6-dodecyl acrylate, respectively. The crude product mixture was then purified by vacuum distillation. The first cut contained primarily acrylic acid, the second cut contained primarily dodecene, and the third cut contained primarily dodecyl acrylate.

Preparation of Pressure Sensitive Adhesive Films

To evaluate select monomers as viable raw materials for pressure sensitive adhesives sample polymers were prepared, as shown in Table 2 below. For example, for Polymer A in Table 2, 37.2 g of 2-ethylhexyl acrylate (BASF, Charlotte, N.C.), 2.8 g of acrylic acid (Alfa Aesar, Ward Hill, Mass.), 0.072 g of 2,2-azobis(2-methyl butyronitrile) (VAZO-67, Sigma-Aldrich, St. Louis, Mo.), and 93 g of ethyl acetate were mixed in a 250 milliliter bottle. This sample was then purged with nitrogen gas for 5 minutes, the bottle was sealed, and then heated to 62° C. for 16 hours. The Mw of the resulting polymer was measured according to Test Method 1 above and recorded in Table 2 below. Polymers B through F were prepared according to Table 2 below following the same procedure as described above with respect to Polymer A. In Polymer B, 2-octyl acrylate (2-OA, prepared as described in U.S. Pat. No. 7,385,020) was used as the primary acrylic monomer.

TABLE 2

| Adhesive | A | B | C | D | E | F |
|---|---|---|---|---|---|---|
| 2EHA (g) | 37.2 | | | | | |
| 2-OA (g) | | 37.2 | | | | |
| Example 4 (g) | | | 37.2 | | | 18.6 |
| Example 5 (g) | | | | 38.4 | | 18.6 |
| Example 6 (g) | | | | | 37.2 | |
| Acrylic Acid (g) | 2.8 | 2.8 | 2.8 | 1.6 | 2.8 | 2.8 |
| VAZO 67 (g) | 0.072 | 0.072 | 0.072 | 0.072 | 0.072 | 0.072 |
| MEK (g) | 93 | 93 | 93 | 93 | 93 | 93 |
| Mw (KDal) | 542.3 | 681.9 | 478.9 | 298.3 | 309.6 | 265.8 |

Comparative Examples 1-2 and Examples 7-11

Pressure Sensitive Films

Comparative Examples 1-2 and Examples 7-11 of pressure sensitive films were evaluated using the following procedure. Prior to coating, samples from Table 2 were mixed with 0.15 wt. % or 0.30 wt. % of 1,1'-isophthaloylbis(2-methylaziridine) (IPBMA, which can be obtained from Pharmten Chemical Co. Leshan, China) crosslinker based on the calculated weight of polymer in the bottle and was mixed for 1 hour. For example, 20 grams of Comparative Example 1 was blended with 0.009 g of 1,1'-isophthaloylbis(2-methylaziridine). Samples were then coated using a knife coater with a set gap of 10 mils (254 micrometers (m)) onto a primed PET backing (MIT 3SAB, Mitsubishi Films, Greer S.C.) that was approximately 2 mils (50.8 μm) thick. Films were then dried in an oven set at 70° C. for approximately 20 minutes to remove the solvent in each coating and yield a dry adhesive film with thickness of 2 mils (50.8 μm). Adhesive films were allowed to age two days at 25° C. and then tested according to Test Methods 2 and 3 above. Adhesive performance results are recorded in Table 3 below.

TABLE 3

| Example | Polymer Used | Added IPBMA (wt. %) | 180° Peel Adhesion (oz./in) | 70° C. Shear Holding (minutes) |
|---|---|---|---|---|
| C. Ex. 1 | A | 0.15 | 57.6 | +10,000 |
| C. Ex. 2 | B | 0.15 | 58.6 | +10,000 |
| Ex. 7 | C | 0.15 | 60.7 | +10,000 |
| Ex. 8 | D | 0.15 | 0.53 | +10,000 |
| Ex. 9 | E | 0.15 | 20.4 | 2 |
| Ex. 10 | E | 0.30 | 23.0 | 15 |
| Ex. 11 | F | 0.15 | 6.1 | 63.5 |

While the specification has been described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A method of making a mixture of structural isomers of a secondary alkyl(meth)acrylate of Formula (I):

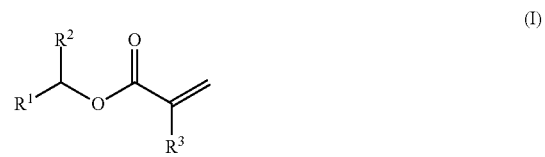

wherein:
$R^1$ and $R^2$ are each independently a $C_1$ to $C_{20}$ saturated linear alkyl group;
the sum of the number of carbons in $R^1$ and $R^2$ is 2 to 21; and
$R^3$ is H or $CH_3$;
wherein the method comprises:
dehydrating a biobased $C_2$-$C_{22}$ alcohol derived from at least one plant oil with a first acid catalyst using a continuous process, thereby forming a mixture of olefins, the first acid catalyst comprising a sulfonated styrene divinylbenzene copolymer; and
reacting (meth)acrylic acid with at least some of the mixture of olefins in the presence of a second acid catalyst comprising a sulfonated styrene divinylbenzene copolymer.

2. The method of claim 1 wherein the first acid catalyst comprises a cation exchange resin.

3. The method of claim 1 wherein the mixture of olefins comprises between 80% and 100% by weight biobased olefins, as determined using ASTM D6866-12.

4. The method of claim 1 wherein the dehydrating occurs at a temperature of 150° C. to 190° C.

5. The method of claim 1 wherein the $C_2$-$C_{22}$ alcohol comprises a $C_8$ alcohol, a $C_{10}$ alcohol, or a $C_{12}$ alcohol.

6. The method of claim 1 wherein the dehydrating is performed in a continuous reactor at a temperature of 150° C. to 190° C. and at a constant weight hourly space velocity (WHSV) of 0.5 $h^{-1}$ to 10 $h^{-1}$, wherein the WHSV is a ratio of mass flow of the $C_2$-$C_{22}$ alcohol entering the system per hour to the mass of the first acid catalyst.

7. The method of claim 1 wherein the dehydrating is performed in a continuous reactor at a temperature of 150° C. to 190° C. and combination of the mixture of olefins and water is produced at a rate of 0.5 g $h^{-1}$ to 10 g $h^{-1}$ per gram of the first acid catalyst.

* * * * *

UNITED STATES PATENT AND TRADEMARK OFFICE
CERTIFICATE OF CORRECTION

PATENT NO. : 9,908,837 B2
APPLICATION NO. : 14/769850
DATED : March 6, 2018
INVENTOR(S) : Joshua Colby Page 1 of 1

It is certified that error appears in the above-identified patent and that said Letters Patent is hereby corrected as shown below:

In the Specification

Column 8,
Line 28, after "funnel" insert -- . --.

Column 10,
Line 12, delete "g s⁻)" and insert -- $g\ s^{-1}$) --, therefor.

Column 13,
Line 59, delete "$R^2$is" and insert -- $R^2$ is --, therefor.
Line 67, delete "$R^2$is" and insert -- $R^2$ is --, therefor.

Column 17,
Line 43, delete "pyrogallo1" and insert -- pyrogallol --, therefor.

Column 31,
Line 31, after "min⁻¹" insert -- . --.
Line 37, delete "(6.05×10" and insert -- $(6.05\times 10^{-4}$ --, therefor.

Column 32,
Line 17, delete "min⁻¹" and insert -- $min^{-1}$ --, therefor.

Column 33,
Line 39, delete "(m))" and insert -- (μm)) --, therefor.

Signed and Sealed this
Seventeenth Day of April, 2018

Andrei Iancu
*Director of the United States Patent and Trademark Office*